US012421441B1

(12) United States Patent
Dowaidar et al.

(10) Patent No.: US 12,421,441 B1
(45) Date of Patent: Sep. 23, 2025

(54) METHOD FOR MICROBIALLY ENHANCED OIL RECOVERY

(71) Applicant: King Fahd University of Petroleum and Minerals, Dhahran (SA)

(72) Inventors: Moataz Mohamed Hamed Abdelmoneim Dowaidar, Dhahran (SA); Saravanan Sankaran Sankaran, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 19/211,847

(22) Filed: May 19, 2025

(51) Int. Cl.
| | | |
|---|---|---|
| C09K 8/582 | (2006.01) | |
| C02F 3/34 | (2023.01) | |
| C12N 1/20 | (2006.01) | |
| E21B 43/16 | (2006.01) | |
| C02F 101/32 | (2006.01) | |

(Continued)

(52) U.S. Cl.
CPC .............. *C09K 8/582* (2013.01); *C02F 3/344* (2013.01); *C02F 3/348* (2013.01); *C12N 1/20* (2013.01); *E21B 43/16* (2013.01); *C02F 2101/32* (2013.01); *C02F 2103/10* (2013.01); *C02F 2305/06* (2013.01); *E21B 43/34* (2013.01)

(58) Field of Classification Search
CPC .......... C09K 8/582; C02F 3/344; C02F 3/348; C02F 2101/32; C02F 2103/10; C02F 2305/06; C12N 1/20; E21B 43/16; E21B 43/34
See application file for complete search history.

(56) References Cited

U.S. PATENT DOCUMENTS

| | | | | |
|---|---|---|---|---|
| 4,522,261 A | * | 6/1985 | McInerney | ............ C09K 8/905 166/305.1 |
| 4,905,761 A | * | 3/1990 | Bryant | ...................... C09K 8/58 435/252.4 |

(Continued)

FOREIGN PATENT DOCUMENTS

| | | |
|---|---|---|
| CN | 101760442 B | 6/2012 |
| CN | 102050523 B | 7/2012 |
| CN | 114480294 B | 1/2024 |

OTHER PUBLICATIONS

J.L. Navarrete-Bolaños, et al., "A Biotechnological Insight to Recycle Waste: Analyzing the Spontaneous Fermentation of Shrimp Waste to Design the Hydrolysis Process of Chitin Into N-Acetylglucosamine", Revista Mexicana de Ingeniería Química, vol. 19, No. 1, May 22, 2019, pp. 263-274.

*Primary Examiner* — Benjamin F Fiorello
(74) *Attorney, Agent, or Firm* — Oblon, McClelland, Maier &Neustadt, L.L.P.

(57) ABSTRACT

A method for the bioremediation of hydrocarbon-contaminated production water through the microbiological process of culturing salt-tolerant bacteria in a high-salt cell culture medium for decontamination. The high-salt cell culture medium contains sodium chloride, sodium sulfate, sodium bicarbonate, calcium chloride, and calcium chloride, along with agar, water, and salt-tolerant bacteria to form broth. Once incubated to form an inoculation mixture, this broth is combined with production water to produce a bacteria-containing liquid mixture, and then treated with production water, bioremediating by propagating the bacteria-containing liquid mixture in the treated production water.

20 Claims, 11 Drawing Sheets

(51) Int. Cl.
*C02F 103/10* (2006.01)
*E21B 43/34* (2006.01)

(56) References Cited

U.S. PATENT DOCUMENTS

| | | | | |
|---|---|---|---|---|
| 5,044,435 A | * | 9/1991 | Sperl | C09K 8/905 |
| | | | | 435/282 |
| 8,783,345 B2 | * | 7/2014 | Babcock | E21B 43/16 |
| | | | | 166/265 |
| 8,863,855 B2 | * | 10/2014 | Kotlar | C09K 8/582 |
| | | | | 166/402 |
| 9,637,721 B2 | | 5/2017 | Elhofy et al. | |
| 9,869,166 B2 | * | 1/2018 | Kohr | E21B 43/20 |
| 10,023,782 B2 | * | 7/2018 | Wang | C09K 8/12 |
| 2020/0071600 A1 | * | 3/2020 | Farmer | C09K 8/582 |
| 2020/0071603 A1 | * | 3/2020 | Farmer | C09K 8/524 |
| 2020/0123885 A1 | * | 4/2020 | Yamamoto | E21B 43/16 |
| 2021/0301191 A1 | * | 9/2021 | Farmer | C09K 8/584 |

* cited by examiner

METHOD FOR MICROBIALLY ENHANCED OIL RECOVERY

BACKGROUND

Technical Field

The present disclosure relates to a method of microbially enhanced oil recovery and a method of bioremediation of hydrocarbon-contaminated water, each using salt-tolerant bacteria.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The increased use of hydrocarbon and petroleum products as primary energy sources contributed to the increase in pollution caused by these contaminants. When these pollutants escape into the environment, they cause soil and freshwater pollution on land due to their seepage and leakage into the ground and water. During oil spills, the hydrocarbon and petrochemical spills pose a hazard to the environment and marine life and also cause numerous ailments like cancers and neural disorders. Therefore, removing or deleting these pollutants before their hazardous effects deteriorate the environment is critical. Although multiple mechanical, thermal, and chemical methods for removing hydrocarbons from polluted areas have been used in the past, most of these methods are ineffective and expensive.

Bioremediation techniques hold great promise as they provide an economical and eco-friendly mechanism for removing petrochemical and hydrocarbon residues from the affected sites. This is achieved by the transformation and/or breakdown of complex organic pollutants into simpler compounds by biological agents such as bacteria, fungi, etc. As shown in Table 1, many naturally occurring microbes present in nature have been identified as being capable of degradation and detoxification of various hydrocarbons and similar contaminants.

TABLE 1

| Examples of Genera That Degrade Oil | | |
|---|---|---|
| Microorganism | Genera | Oil component |
| Bacteria | Alcanivorax | n-alkanes (C8-C32) |
| | Actinomyces | n-alkanes |
| | Bacillusa | n-alkanes (C13-C30) and aromatics |
| | Gordonia | n-alkanes |
| | Marinobacter | n-alkanes |
| | Pseudomonas | n-alkanes (C14-C30) and resins |
| Cyanobacteria | Anabaena | n-alkanes |
| | Aphanocapsa | n-alkanes and aromatics |
| | Microcoleus | aromatics |
| | Oscillatoria | aromatics |
| | Nostoc | aromatics |
| | Plectonema | n-alkanes and aromatics |
| Algae And Diatoms | Amphora | aromatics |
| | Chlamydomonas | aromatics |
| | Chlorella | aromatics |
| | Dunaliella | aromatics |

TABLE 1-continued

| Examples of Genera That Degrade Oil | | |
|---|---|---|
| Microorganism | Genera | Oil component |
| Fungi | Prototheca | aromatics |
| | Ulva | aromatics |
| | Aspergillus | n-alkanes and aromatics |
| | Candida | n-alkanes and aromatics |
| | Fusarium | n-alkanes and aromatics |
| | Penicillium | n-alkanes (C11-C25) and aromatics |
| | Trichoderma | n-alkanes and aromatics |

Although numerous microorganisms, enzymes, biosurfactants, nanomaterials, genetically modified strains, and plant life have been used for bioremediation, most conventional methods are inefficient and slow degradation rate due to harsh environmental conditions, thereby necessitating the need for developing new methods to boost the bioremediation process. Further, these methods typically require a narrow range of environmental conditions. For example, a microbe may not tolerate an area that is too cold, too warm, or even exposure to oxygen. Many hydrocarbon environmental contamination events take place in or involve water having a high salt concentration. Microbes suitable for terrestrial or freshwater use may not be available if an oil spill occurs at sea, for example. In addition, contemporary oil and gas production operations can involve the use of or generate very high salt concentration brines (e.g., production water). An environmental contamination event that involves such brines may preclude the use of many bioremediation techniques. Accordingly, an object of the present disclosure is to develop a method that allows for accelerated biodegradation of hydrocarbons in a simple and cost-effective manner and which may be compatible with a wide variety of environmental conditions.

SUMMARY

According to a first aspect, the present disclosure relates to a method of bioremediating a hydrocarbon-contaminated production water. In some embodiments, the method includes the treatment of hydrocarbon-contaminated water to separate a majority of the hydrocarbons present in the hydrocarbon-contaminated production water to form a treated production water; and culturing a salt-tolerant bacteria using a high-salt cell culture medium. In some embodiments, the composition of the high-salt cell culture medium includes: sodium chloride present in an amount of 140 to 160 g per liter of high-salt cell culture medium; sodium sulfate present in an amount of 0.40 to 0.60 g per liter of high-salt cell culture medium; sodium bicarbonate present in an amount of 0.38 to 0.59 g per liter of high-salt cell culture medium; calcium chloride present in an amount of 60 to 80 g per liter of high-salt cell culture medium; magnesium chloride present in an amount of 10 to 31 g per liter of high-salt cell culture medium; agar present in an amount of 10 to 30 g per liter of high-salt cell culture medium, glycerol present in an amount of 1 to 5 vol %, and water, each based on a total volume of high-salt cell culture medium. In some embodiments, the method further includes suspending the salt-tolerant bacteria in a liquid medium comprising sodium chloride present in an amount of 140 to 160 g per liter of the liquid medium; sodium sulfate present in an amount of 0.40 to 0.60 g per liter of the liquid medium; sodium bicarbonate present in an amount of 0.38 to 0.59 g per liter of the liquid medium; calcium chloride present in an amount of 60 to 80 g per liter of the liquid medium; magnesium chloride present in an amount of 10 to 31 g per liter of the liquid medium, glycerol present in an amount of 1 to 5 vol %, and water, each based on a total volume of the liquid medium, to form a first broth. In some embodiments, the method further includes incubating the first broth to form an inoculation mixture; mixing the inoculation mixture with production water in a volume ratio of 1:1 to form a bacteria-containing liquid mixture; and bioremediating the treated production water by propagating the bacteria-containing liquid mixture in the treated production water.

In some embodiments, the method further includes producing a production mixture comprising hydrocarbons and water from a subterranean geological formation. In some embodiments, the treating includes separating a first amount of the hydrocarbons from the production mixture by gravity separation and skimming to form the treated production water comprising hydrocarbons dissolved in water and hydrocarbons dispersed in water in the form of droplets having a size of 0.1 mm or less. In some embodiments, the bioremediating includes mixing the treated production water and the bacteria-containing liquid mixture and circulating in a holding tank having an open top exposed to sunlight with a residence time of 2-3 days. In some embodiments, the high-salt cell culture medium further includes a nutrient supplement which is at least one selected from a group consisting of a mixture of plant oils comprising 12.5 to 17.5 wt. % saturated fatty acids, 17.5 to 22.5 wt. % monounsaturated fatty acids, 25 to 35 wt. % polyunsaturated fatty acids, and triglycerides, each based on a total weight of plant oil mixture; and a nutrient mixture comprising 2 to 4 g peptone per liter of high-salt cell culture medium, and 4.0 to 6.0 g yeast extract per liter of high-salt cell culture medium.

In some embodiments, the plant oil mixture present in an amount of 0.25 to 2.5 vol. % based on a total volume of high-salt cell culture medium.

In some embodiments, the method further includes deoxygenating the high-salt cell culture medium by bubbling nitrogen gas which is substantially free of oxygen through the high-salt cell culture medium before culturing the salt-tolerant bacteria.

In some embodiments, the method further includes sterilizing the high-salt cell culture medium by autoclaving a non-sterile volume of the high-salt cell culture medium at 115 to 130° C. and 5 to 25 psi for 10 to 60 minutes before culturing the salt-tolerant bacteria.

In some embodiments, the method of culturing the salt-tolerant bacteria is performed at 40 to 70° C. for 1 to 14 days.

In some embodiments, the method of culturing the salt-tolerant bacteria is performed under anaerobic conditions.

In some embodiments, the high-salt cell culture medium further comprises crude oil present in an amount of 0.25 to 2.5 vol. % based on a total volume of high-salt cell culture medium.

In some embodiments, the liquid medium also includes a nutrient supplement which is at least one selected from the group consisting of a plant oil mixture with 12.5 to 17.5 wt. % saturated fatty acids, 17.5 to 22.5 wt. % monounsaturated fatty acids, 25 to 35 wt. % polyunsaturated fatty acids, and triglycerides, each based on a total weight of plant oil mixture; and a nutrient mixture comprising 2 to 4 g peptone per liter of liquid medium, and 4.0 to 6.0 g yeast extract per liter of liquid medium.

In some embodiments, the plant oil mixture present in an amount of 0.25 to 2.5 vol. % based on a total volume of liquid medium.

In some embodiments, the method of incubating the first broth is performed at 45 to 75° C. for 30 to 120 days.

In some embodiments, the method of incubating the first broth is performed under anaerobic conditions.

In some embodiments, the liquid medium further comprises crude oil present in an amount of 1 to 40 vol % based on a total volume of liquid medium.

In some embodiments, the method further includes prior to the incubating the first broth, deoxygenating the liquid medium by bubbling nitrogen gas which is substantially free of oxygen through the liquid medium.

In some embodiments, the method involves prior to the incubating the first broth, sterilizing the liquid medium by autoclaving a non-sterile volume of the liquid medium at 115 to 130° C. and 5 to 25 pounds per square inch (psi) for 10 to 60 minutes.

In some embodiments, the production water has a salinity of 350,000 parts per million (ppm) to 5,000,000 ppm.

In some embodiments, the method further includes propagating the bacteria-containing liquid mixture in the treated production water, and then bubbling through the treated production water nitrogen gas which is substantially free of oxygen.

In some embodiments, the method includes adding a nutrient supplement to the treated production water which is at least one selected from the group consisting of a plant oil mixture having 12.5 to 17.5 wt. % saturated fatty acids, 17.5 to 22.5 wt. % monounsaturated fatty acids, 25 to 35 wt. % polyunsaturated fatty acids, and triglycerides, each based on a total weight of plant oil mixture; and a nutrient mixture comprising 2 to 4 g peptone per liter of nutrient supplement, and 4.0 to 6.0 g yeast extract per liter of nutrient supplement.

In some embodiments, the salt-tolerant bacteria is a member of a genus selected from *streptococcus, bacillus*, and *halomonas*.

In some embodiments, the bacteria-containing liquid mixture includes a salt-tolerant bacteria selected from the genus *streptococcus*, a salt-tolerant bacteria from the genus *bacillus*, and a salt-tolerant bacteria from the genus *halomonas*.

The present disclosure also relates to a method of microbially enhanced oil recovery. In some embodiments, the method comprises culturing a salt-tolerant bacteria using a high-salt cell culture medium. In some embodiments, the high-salt cell culture medium comprises sodium chloride present in an amount of 140 to 160 g per liter of high-salt cell culture medium, sodium sulfate present in an amount of 0.40 to 0.60 g per liter of high-salt cell culture medium, sodium bicarbonate present in an amount of 0.38 to 0.59 g per liter of high-salt cell culture medium, calcium chloride present in an amount of 60 to 80 g per liter of high-salt cell culture medium, magnesium chloride present in an amount of 10 to 31 g per liter of high-salt cell culture medium, agar present in an amount of 10 to 30 g per liter of high-salt cell culture medium, glycerol present in an amount of 1 to 5 vol %, and water, each based on a total volume of high-salt cell culture medium. In some embodiments, the method comprises suspending the salt-tolerant bacteria in a liquid medium. In some embodiments, the liquid medium comprises sodium chloride present in an amount of 140 to 160 g per liter of liquid medium, sodium sulfate present in an amount of 0.40 to 0.60 g per liter of liquid medium, sodium bicarbonate present in an amount of 0.38 to 0.59 g per liter of liquid medium, calcium chloride present in an amount of 60 to 80 g per liter of liquid medium, magnesium chloride present in an amount of 10 to 31 g per liter of liquid medium, glycerol present in an amount of 1 to 5 vol %, and water, each based on a total volume of liquid medium, to form a first broth. In some embodiments, the method comprises incubating the first broth to form an inoculation mixture. In some embodiments, the method comprises mixing the inoculation mixture with a production water in a volume ratio of 1:1 to form a bacteria-containing liquid mixture. In some embodiments, the method comprises propagating the bacteria-containing liquid mixture in a portion of a subterranean geological formation containing an oil deposit. In some embodiments, the method comprises recovering oil in the oil deposit.

In some embodiments, the recovering comprises producing a production mixture comprising the oil in the oil deposit the bacteria-containing liquid mixture, recovering to a surface the production mixture, and separating the oil and the bacteria-containing liquid mixture. In some embodiments, the high-salt cell culture medium further comprises a nutrient supplement which is at least one selected from the group consisting of a plant oil mixture comprising 12.5 to 17.5 wt. % saturated fatty acids, 17.5 to 22.5 wt. % monounsaturated fatty acids, 25 to 35 wt. % polyunsaturated fatty acids, and triglycerides, each based on a total weight of plant oil mixture; and a nutrient mixture comprising 2 to 4 g peptone per liter of high-salt cell culture medium, and 4.0 to 6.0 g yeast extract per liter of high-salt cell culture medium.

In some embodiments, the plant oil mixture present in an amount of 0.25 to 2.5 vol. % based on a total volume of high-salt cell culture medium.

In some embodiments, the method further comprises, prior to the culturing, deoxygenating the high-salt cell culture medium by bubbling nitrogen gas which is substantially free of oxygen through the high-salt cell culture medium.

In some embodiments, the method further comprises, prior to the culturing, sterilizing the high-salt cell culture medium by autoclaving a non-sterile volume of the high-salt cell culture medium at 115 to 130° C. and 5 to 25 psi for 10 to 60 minutes.

In some embodiments, the culturing is performed at 40 to 70° C. for 1 to 14 days.

In some embodiments, the culturing is performed under anaerobic conditions.

In some embodiments, the high-salt cell culture medium further comprises crude oil present in an amount of 0.25 to 2.5 vol. % based on a total volume of high-salt cell culture medium.

In some embodiments, the liquid medium further comprises a nutrient supplement which is at least one selected from the group consisting of a plant oil mixture comprising 12.5 to 17.5 wt. % saturated fatty acids, 17.5 to 22.5 wt. % monounsaturated fatty acids, 25 to 35 wt. % polyunsaturated fatty acids, and triglycerides, each based on a total weight of plant oil mixture; and a nutrient mixture comprising 2 to 4 g peptone per liter of liquid medium, and 4.0 to 6.0 g yeast extract per liter of liquid medium.

In some embodiments, the plant oil mixture present in an amount of 0.25 to 2.5 vol. % based on a total volume of liquid medium.

In some embodiments, the incubating is performed at 45 to 75° C. for 30 to 120 days.

In some embodiments, the incubating is performed under anaerobic conditions.

In some embodiments, the liquid medium further comprises crude oil present in an amount of 1 to 40 vol. % based on a total volume of liquid medium.

In some embodiments, the method further comprises, prior to the incubating, deoxygenating the liquid medium by bubbling nitrogen gas which is substantially free of oxygen through the liquid medium.

In some embodiments, the method further comprises, prior to the incubating, sterilizing the liquid medium by autoclaving a non-sterile volume of the liquid medium at 115 to 130° C. and 5 to 25 psi for 10 to 60 minutes.

In some embodiments, the production water has a salinity of 350,000 ppm to 5,000,000 ppm.

In some embodiments, the method further comprises, following the propagating the bacteria-containing liquid mixture in a portion of a subterranean geological formation containing an oil deposit, pumping into the subterranean geological formation nitrogen gas which is substantially free of oxygen.

In some embodiments, the method further comprises adding to the production water a nutrient supplement which is at least one selected from the group consisting of a plant oil mixture comprising 12.5 to 17.5 wt. % saturated fatty acids, 17.5 to 22.5 wt. % monounsaturated fatty acids, 25 to 35 wt. % polyunsaturated fatty acids, and triglycerides, each based on a total weight of plant oil mixture; and a nutrient mixture comprising 2 to 4 g peptone per liter of nutrient supplement, and 4.0 to 6.0 g yeast extract per liter of nutrient supplement.

In some embodiments, the salt-tolerant bacteria is a member of a genus selected from *streptococcus, bacillus*, and *halomonas*.

In some embodiments, the bacteria-containing liquid mixture comprises a salt-tolerant bacteria from the genus *streptococcus*, a salt-tolerant bacteria from the genus *bacillus*, and a salt-tolerant bacteria from the genus *halomonas*.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
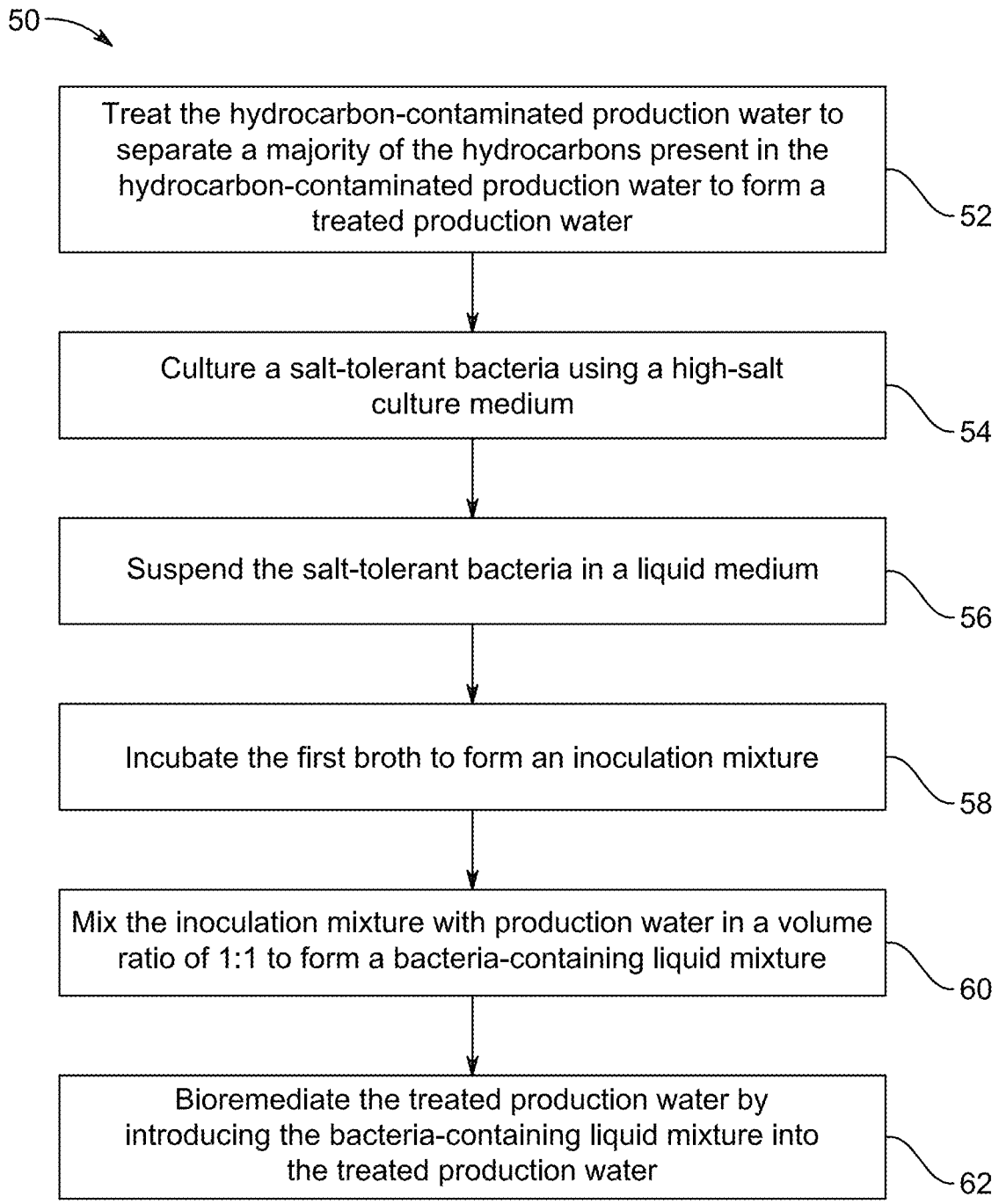
FIG. 1 is a flowchart of a method for bioremediating a hydrocarbon-contaminated water, according to certain embodiments.

In the drawings, reference numerals designate identical or corresponding parts throughout the several views. Further, as used herein, the words "a," "an" and the like generally carry a meaning of "one or more," unless stated otherwise.

As used herein, the words "about," "approximately," or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), or +/−20% of the stated value (or range of values). Within the description of this disclosure, where a numerical limit or range is stated, the endpoints are included unless stated otherwise. Also, all values and subranges within a numerical limit or range are specifically included as if explicitly written out.

The term "culturing" refers to a process of growing organisms (including microorganisms or cells) outside of their natural environment under controlled conditions. Culturing can involve the isolation of the organism from a source such as a living tissue or environmental source. Culturing typically involves providing to the organisms sufficient nutrients to sustain their life and growth. Culturing can include the introduction of certain agents that can modify the organism from a natural version of the organism. Culturing can include enrichment. Enrichment can involve specific nutrients, agents, or conditions to increase or decrease a particular amount of a certain organism compared to other organisms which may be present. For example, enrichment can promote the growth of one particular type of organism while suppressing the growth of other organisms. Enrichment can be used to produce a population of organisms which is different from a population present in an environmental source.

A hydrocarbon is defined as a chemical compound including hydrogen and carbon atoms. These compounds are fundamental to organic chemistry and are typically categorized into distinct groups based on their molecular structure, including alkanes, alkenes, alkynes, and aromatic hydrocarbons. Hydrocarbons occur abundantly in nature, notably as constituents of fossil fuels such as petroleum and natural gas. They are also present in living organisms that serve as integral components of fats, oils, and waxes. It should be understood that as used herein, the term also includes compounds of hydrogen and carbon that include other elements common encountered in organic molecules as well, such as oxygen, nitrogen, sulfur, phosphorus, and halogens such as chlorine and bromine.

"Production water" or "produced water" refers to water that is produced as a byproduct during the extraction of oil and natural gas. Production water is generally brackish and saline water in nature. Oil and gas reservoirs often have water in addition to hydrocarbons, sometimes as a separate fluid beneath the oil and gas, and sometimes in the same area with the oil and gas. Oil wells sometimes produce large volumes of water with the oil, while gas wells tend to produce water in smaller proportions. Further, water may be injected into an oil or gas well, for example to drive to produce hydrocarbons. This process may be referred to as "waterflooding" and often involves injecting water into the oil or gas reservoirs to increase pressure or displace the hydrocarbons. In offshore areas, sea water is used. In onshore installations, the injected water is typically obtained from rivers, treated produced water, or underground.

Production water typically contains dissolved or suspended hydrocarbons, dissolved gases, dissolved solutes such as salts, and suspended particulates such as mud or rock. Further, injected water may be treated with many chemicals to make it suitable for injection and these chemicals may be present in the production water as well.

Saturated fatty acids are a class of fatty acids characterized by carbon chains where all available carbon bonds are single bonds (saturated with hydrogen atoms). This results in a straight molecular structure without double bonds. Typically, saturated fatty acids are solid at room temperature. Saturated fatty acids are typically found in animal and solid vegetable fats (e.g., butter, lard, coconut oil) and are typically less prone to oxidation than unsaturated fatty acids.

Monounsaturated fatty acids (MUFA) are a category of fatty acids characterized by the presence of a single double bond within their carbon chain. This double bond is typically in the cis configuration, resulting in a kink in the molecule's structure. MUFA are predominantly found in plant-based oils such as olive oil, canola oil, and avocado oil, as well as in certain animal fats.

Polyunsaturated fatty acids are fatty acids that contain two or more double bonds in their hydrocarbon chain. These double bonds create multiple kinks in the molecule, which may contribute to fluidity and flexibility. PUFA are essential nutrients that are frequently important to human and animal diets. Examples include omega-3 fatty acids (alpha-linolenic acid, EPA, and DHA) and omega-6 fatty acids (linoleic acid and arachidonic acid).

Triglycerides are the most common fat in foods and living organisms. They comprise glycerol and three fatty acid molecules joined by ester bonds. Triglycerides are a significant energy source for a wide variety of organisms. Triglycerides can include any mixture of saturated, monounsaturated, or polyunsaturated fatty acids attached to the glycerol backbone.

As used herein "biodegradation" refers to the breakdown of a substance or material by chemical, biochemical, or biological processes, that are associated with living organisms. Biodegradation can be performed by any suitable chemical or biochemical substance present in, produced by, or otherwise associated with the living organism. Typically, biodegradation involves the action of one or more enzymes. Biodegradation breaks the substance or material into smaller and/or chemically simpler units. For example, biodegradation of a long-chain hydrocarbon can result in the formation of two or more hydrocarbons each having a shorter chain. Biodegradation can involve various chemical transformations, such as the introduction or removal of carbon atoms, hydrogen atoms, oxygen atoms, nitrogen atoms, and the like.

According to a first aspect, the present disclosure relates to a bioremediation method for treating water contaminated with hydrocarbons.

In general, the hydrocarbons can be or include any hydrocarbons known to one of ordinary skill in the art. Examples of such hydrocarbons include, but are not limited to, alkanes, olefins, waxes, tars, creosote, crude oil, refined oil, fuel oils, diesel oils, gasoline, hydraulic oils, kerosene, chrysene, cresol, cyclohexanone, ethylbenzene, butyl benzene, ethyl acetate, fluorine, isoprenoids, methyl ethylacetate, 2-butanone, methyl pentanone, methyl propylacetate, butylacetate, petroleum oils and greases, phenanthrene, phenol, solvents, mineral spirits, terpene-based compounds, phthalates such as bis(2) ethylhexylphthalate and/or dioctylphthalate, phenolic compounds, and/or combination thereof. Of particular relevance to the present disclosure are crude oil, refined oil/petroleum, and natural gas.

FIG. 1 illustrates a schematic flow chart of a method 50 of bioremediating a hydrocarbon-contaminated production water. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes treating the hydrocarbon-contaminated production water to separate most of the hydrocarbons present in the hydrocarbon-contaminated production water to form a treated production water. In general, any suitable method of separating hydrocarbons from water may be used. Examples of such suitable methods include, but are not limited to, gravity separation (e.g., using a separating funnel), centrifugation, filtration, coalescence, skimming (e.g., using a skim tank), cyclonic separation (e.g., using a deoiling cyclone), gas flotation, and membrane filtration. Typically, these methods use the fact that hydrocarbons are less dense than water and will naturally rise to the surface, allowing for separation.

In some embodiments, the production water and/or hydrocarbon-contaminated is highly saline. In some embodiments, the production water has a salinity of 50,000 ppm to 5,000,000 ppm. For example, the production water may have a salinity of 50,000 ppm, 75,000 ppm, 100,000 ppm, 125,000 ppm, 150,000 ppm, 175,000 ppm, 200,000 ppm, 225,000 ppm, 250,000 ppm, 275,000 ppm, 300,000 ppm, 325,000 ppm, 350,000 ppm, 375,000 ppm, 400,000 ppm, 425,000 ppm, 450,000 ppm, 475,000 ppm, 500,000 ppm, 525,000 ppm, 550,000 ppm, 575,000 ppm, 600,000 ppm, 625,000 ppm, 650,000 ppm, 675,000 ppm, 700,000 ppm, 725,000 ppm, 750,000 ppm, 775,000 ppm, 800,000 ppm, 825,000 ppm, 850,000 ppm, 875,000 ppm, 900,000 ppm, 925,000 ppm, 950,000 ppm, 975,000 ppm, 1,000,000 ppm, 1,250,000 ppm, 1,500,000 ppm, 1,750,000 ppm, 2,000,000 ppm, 2,250,000 ppm, 2,500,000 ppm, 2,750,000 ppm, 3,000,000 ppm, 3,250,000 ppm, 3,500,000 ppm, 3,750,000 ppm, 4,000,000 ppm, 4,250,000 ppm, 4,500,000 ppm, 4,750,000 ppm, or 5,000,000 ppm.

In some embodiments, the hydrocarbon-contaminated production water is treated to remove particulates, dissolved solids, and other non-water, non-hydrocarbon impurities. In general, such removal may be performed by any suitable method or combination of methods, including physical (membrane filtration, gravity separation, decantation, adsorption, skimming, etc.), chemical (precipitation, oxidation), and biological (activated sludge, biological aerated filters, and others) methods.

In some embodiments, the hydrocarbon-contaminated production water is treated to remove a majority (e.g., greater than 50%) of hydrocarbons present. In general, such removal may be performed by any suitable method or combination of methods, including physical (membrane filtration, adsorption, etc.), chemical (precipitation, oxidation), and biological (activated sludge, biological aerated filters, and others) methods. For example, oil may be skimmed or removed via application of an adsorbent prior to performing other steps of the method. In some embodiments, the production water is treated to remove at least 50%, at least 52.5%, at least 55%, at least 57.5%, at least 60%, at least 62.5%, at least 65%, at least 67.5%, at least 70%, at least 72.5%, at least 75%, at least 77.5%, at least 80%, at least 82.5%, at least 85%, at least 87.5%, at least 90% of an initial amount of hydrocarbons present. Such an amount may be measured by any suitable means, such as by mass, volume, or mole %.

In some embodiments, the method further includes producing a production mixture comprising hydrocarbons and water from a subterranean geological formation. In some embodiments, the treating includes separating a first amount of the hydrocarbons from the production mixture to form the treated production water. Such separating can be performed by any suitable method as described above. For example, the separating can be performed by gravity separation and/or skimming.

In some embodiments, the treated production water comprises hydrocarbons. In some embodiments, the treated production water comprises hydrocarbons dissolved in water. In some embodiments, the treated production water comprises hydrocarbons dispersed in water in the form of droplets having a size of 0.1 mm or less. In some embodiments, the treated production water comprises hydrocarbons present in an amount of 50 to 100,000 ppm. For example, the hydrocarbons may be present in the treated production water in an amount of 50 ppm, 100 ppm, 150 ppm, 200 ppm, 250 ppm, 300 ppm, 350 ppm, 400 ppm, 450 ppm, 500 ppm, 550 ppm, 600 ppm, 650 ppm, 700 ppm, 750 ppm, 800 ppm, 850 ppm, 900 ppm, 950 ppm, 1000 ppm, 1100 ppm, 1200 ppm, 1300 ppm, 1400 ppm, 1500 ppm, 1600 ppm, 1700 ppm, 1800 ppm, 1900 ppm, 2000 ppm, 2250 ppm, 2500 ppm, 2750 ppm, 3000 ppm, 3250 ppm, 3500 ppm, 3750 ppm, 4000 ppm, 4250 ppm, 4500 ppm, 4750 ppm, 5000 ppm, 5250 ppm, 5500 ppm, 5750 ppm, 6000 ppm, 6250 ppm, 6500 ppm, 6750 ppm, 7000 ppm, 7250 ppm, 7500 ppm, 7750 ppm, 8000 ppm, 8250 ppm, 8500 ppm, 8750 ppm, 9000 ppm, 9250 ppm, 9500 ppm, 9750 ppm, 10,000 ppm, 11,000 ppm, 12,000 ppm, 13,000 ppm, 14,000 ppm, 15,000 ppm, 16,000 ppm, 17,000 ppm, 18,000 ppm, 19,000 ppm, 20,000 ppm, 25,000 ppm, 30,000 ppm, 35,000 ppm, 40,000 ppm, 45,000 ppm, 50,000 ppm, 55,000 ppm, 60,000 ppm, 65,000 ppm, 70,000 ppm, 75,000 ppm, 80,000 ppm, 85,000 ppm, 90,000 ppm, 95,000 ppm, or 100,000 ppm.

At step 54, the method 50 includes culturing a salt-tolerant bacteria using a high-salt cell culture medium. In some embodiments, the salt-tolerant bacteria is a member of a genus selected from *Streptococcus*, *Bacillus*, and *Halomonas*. In some embodiments, the salt-tolerant bacteria belonging to the genus *Streptococcus* is *Streptococcus pyogenes* and/or *Streptococcus pneumoniae*. In some embodiments, the salt-tolerant bacteria belonging to the genus *Bacillus* is *Bacillus anthracis*, and/or *Bacillus subtilis*. In some embodiments, the salt-tolerant bacteria belonging to the genus *Halomonas* is *Halomonas elongate* and/or *Halomonas titanicae*. In some embodiments, other salt-tolerant bacteria capable of hydrocarbon degradation may be used as well, for example, bacteria belonging to the genus *Acinetobacter, Aeromonas, Alcaligenes, Alteromonas, Arthrobacter, Bacillus, Flavobacterium*, Georgfuchsia, Idiomarina, *Klebsiella, Labrenzia, Marinobacter*, Marimonas, Maritimibacter, Methylophaga, Muricauda, Neptunomonas, Novosphingobium, *Nocardia, Oleibacter, Paracoccus*, Pelagibacter, Porticoccus, Pseudoalteromona, *Pseudomonas*, Psycroserpens, Rheinheimera, Rhodobacteria, *Rhodococcus* (high GC group), Roseobacter, Roseovariu, Sarcina, *Shewanella, Sphingomonas*, Sulfitobacteria, Thalassospira, *Vibrio*, and the like. In some embodiments, the choice of bacteria depends on the pollutant/contaminant/hydrocarbon to be degraded. In some embodiments, the choice of bacteria depends on the composition of the production water. In some embodiments, the choice of bacteria depends on the environmental conditions (e.g., aerobic/anaerobic, amount of sunlight, temperature, etc.) where the method is being performed. In some embodiments, the method is performed in an artificial, controlled environment. For example, in a specific indoor facility or other man-made environment. In some embodiments, a single strain belonging to the same genus or two or more strains belonging to the same genus and/or different genera, in equal ratios or different ratios, may be cultured on the high-salt cell culture medium.

In some embodiments, the high-salt cell culture medium includes sodium chloride present in an amount of 140 to 160 g per liter (g/L). For example, the high-salt cell culture medium can include sodium chloride in an amount of 140.0 g/L, 140.5 g/L, 141.0 g/L, 141.5 g/L, 142.0 g/L, 142.5 g/L, 143.0 g/L, 143.5 g/L, 144.0 g/L, 144.5 g/L, 145.0 g/L, 145.5 g/L, 146.0 g/L, 146.5 g/L, 147.0 g/L, 147.5 g/L, 148.0 g/L, 148.5 g/L, 149.0 g/L, 149.5 g/L, 150.0 g/L, 150.5 g/L, 151.0 g/L, 151.5 g/L, 152.0 g/L, 152.5 g/L, 153.0 g/L, 153.5 g/L, 154.0 g/L, 154.5 g/L, 155.0 g/L, 155.5 g/L, 156.0 g/L, 156.5 g/L, 157.0 g/L, 157.5 g/L, 158.0 g/L, 158.5 g/L, 159.0 g/L, 159.5 g/L, or 160.0 g/L. In some embodiments, the high-salt cell culture medium includes sodium chloride present in an amount of 150.46 g per liter of high-salt cell culture medium.

In some embodiments, the high-salt cell culture medium includes sodium sulfate present in an amount of 0.40 to 0.60 g per liter (g/L). For example, the high-salt cell culture medium can include sodium sulfate in an amount of 0.400 g/L, 0.405 g/L, 0.410 g/L, 0.415 g/L, 0.420 g/L, 0.425 g/L, 0.430 g/L, 0.435 g/L, 0.440 g/L, 0.445 g/L, 0.450 g/L, 0.455 g/L, 0.460 g/L, 0.465 g/L, 0.470 g/L, 0.475 g/L, 0.480 g/L, 0.485 g/L, 0.490 g/L, 0.495 g/L, 0.500 g/L, 0.505 g/L, 0.510 g/L, 0.515 g/L, 0.520 g/L, 0.525 g/L, 0.530 g/L, 0.535 g/L, 0.540 g/L, 0.545 g/L, 0.550 g/L, 0.555 g/L, 0.560 g/L, 0.565 g/L, 0.570 g/L, 0.575 g/L, 0.580 g/L, 0.585 g/L, 0.590 g/L, 0.595 g/L, or 0.600 g/L. In some embodiments, the high-salt cell culture medium includes sodium sulfate present in an amount of 0.5175 g per liter of high-salt cell culture medium.

In some embodiments, the high-salt cell culture medium includes sodium bicarbonate present in an amount of 0.38 to 0.59 g per liter (g/L). For example, the high-salt cell culture medium can include sodium bicarbonate in an amount of 0.380 g/L, 0.385 g/L, 0.390 g/L, 0.395 g/L, 0.400 g/L, 0.405 g/L, 0.410 g/L, 0.415 g/L, 0.420 g/L, 0.425 g/L, 0.430 g/L, 0.435 g/L, 0.440 g/L, 0.445 g/L, 0.450 g/L, 0.455 g/L, 0.460 g/L, 0.465 g/L, 0.470 g/L, 0.475 g/L, 0.480 g/L, 0.485 g/L, 0.490 g/L, 0.495 g/L, 0.500 g/L, 0.505 g/L, 0.510 g/L, 0.515 g/L, 0.520 g/L, 0.525 g/L, 0.530 g/L, 0.535 g/L, 0.540 g/L, 0.545 g/L, 0.550 g/L, 0.555 g/L, 0.560 g/L, 0.565 g/L, 0.570 g/L, 0.575 g/L, 0.580 g/L, 0.585 g/L, or 0.590 g/L. In some embodiments, the high-salt cell culture medium includes sodium bicarbonate present in an amount of 0.4874 g per liter of high-salt cell culture medium.

In some embodiments, the high-salt cell culture medium includes calcium chloride present in an amount of 60 to 80 g per liter (g/L). For example, the high-salt cell culture medium can include calcium chloride in an amount of 60.0 g/L, 60.5 g/L, 61.0 g/L, 61.5 g/L, 62.0 g/L, 62.5 g/L, 63.0 g/L, 63.5 g/L, 64.0 g/L, 64.5 g/L, 65.0 g/L, 65.5 g/L, 66.0 g/L, 66.5 g/L, 67.0 g/L, 67.5 g/L, 68.0 g/L, 68.5 g/L, 69.0 g/L, 69.5 g/L, 70.0 g/L, 70.5 g/L, 71.0 g/L, 71.5 g/L, 72.0 g/L, 72.5 g/L, 73.0 g/L, 73.5 g/L, 74.0 g/L, 74.5 g/L, 75.0 g/L, 75.5 g/L, 76.0 g/L, 76.5 g/L, 77.0 g/L, 77.5 g/L, 78.0 g/L, 78.5 g/L, 79.0 g/L, 79.5 g/L, or 80.0 g/L. In some embodiments, the high-salt cell culture medium includes calcium chloride present in an amount of 69.823 g per liter of high-salt cell culture medium.

In some embodiments, the high-salt cell culture medium includes magnesium chloride present in an amount of 10 to 31 g per liter (g/L). For example, the high-salt cell culture medium can include magnesium chloride in an amount of 10.0 g/L, 10.5 g/L, 11.0 g/L, 11.5 g/L, 12.0 g/L, 12.5 g/L, 13.0 g/L, 13.5 g/L, 14.0 g/L, 14.5 g/L, 15.0 g/L, 15.5 g/L, 16.0 g/L, 16.5 g/L, 17.0 g/L, 17.5 g/L, 18.0 g/L, 18.5 g/L, 19.0 g/L, 19.5 g/L, 20.0 g/L, 20.5 g/L, 21.0 g/L, 21.5 g/L, 22.0 g/L, 22.5 g/L, 23.0 g/L, 23.5 g/L, 24.0 g/L, 24.5 g/L, 25.0 g/L, 25.5 g/L, 26.0 g/L, 26.5 g/L, 27.0 g/L, 27.5 g/L, 28.0 g/L, 28.5 g/L, 29.0 g/L, 29.5 g/L, 30.0 g/L, 30.5 g/L, or 31.0 g/L. In some embodiments, the high-salt cell culture medium includes magnesium chloride present in an amount of 20.395 g per liter of high-salt cell culture medium.

In some embodiments, the high-salt cell culture medium includes agar present in an amount of 10 to 30 g per liter (g/L) based on the total volume of high-salt cell culture medium. For example, the high-salt cell culture medium can include agar in an amount of 10.0 g/L, 10.5 g/L, 11.0 g/L, 11.5 g/L, 12.0 g/L, 12.5 g/L, 13.0 g/L, 13.5 g/L, 14.0 g/L, 14.5 g/L, 15.0 g/L, 15.5 g/L, 16.0 g/L, 16.5 g/L, 17.0 g/L, 17.5 g/L, 18.0 g/L, 18.5 g/L, 19.0 g/L, 19.5 g/L, 20.0 g/L, 20.5 g/L, 21.0 g/L, 21.5 g/L, 22.0 g/L, 22.5 g/L, 23.0 g/L, 23.5 g/L, 24.0 g/L, 24.5 g/L, 25.0 g/L, 25.5 g/L, 26.0 g/L, 26.5 g/L, 27.0 g/L, 27.5 g/L, 28.0 g/L, 28.5 g/L, 29.0 g/L, 29.5 g/L, or 30.0 g/L based on the total volume of high-salt cell culture medium. In some embodiments, the high-salt cell culture medium includes agar present in an amount of 20.0 g/L based on the total volume of high-salt cell culture medium. In some embodiments, the high-salt cell culture medium includes agar present in an amount of 2% by weight based on a total weight of high-salt cell culture medium.

In some embodiments, the high-salt cell culture medium includes glycerol present in an amount of 1 to 5 vol %, based on a total volume of high-salt cell culture medium. For example, the high-salt cell culture medium can include glycerol in an amount of 1.0 wt. %, 1.25 wt. %, 1.5 wt. %, 1.75 wt. %, 2.0 wt. %, 2.25 wt. %, 2.5 wt. %, 2.75 wt. %, 3.0 wt. %, 3.25 wt. %, 3.5 wt. %, 3.75 wt. %, 4.0 wt. %, 4.25 wt. %, 4.5 wt. %, 4.75 wt. %, or 5.0 wt. %, based on a total volume of high-salt cell culture medium.

In some embodiments, the high-salt cell culture medium includes water. In some embodiments, the high-salt cell culture medium is a solid medium. In some embodiments, the high-salt cell culture medium is a gel medium.

In some embodiments, the high-salt cell culture medium further includes a nutrient supplement that is at least one selected from the group consisting of a plant oil mixture and a nutrient mixture.

In some embodiments, the plant oil mixture is present in an amount of 0.25 to 2.5 vol % based on the total volume of the high-salt cell culture medium. For example, the plant oil mixture may be present in an amount of 0.250 vol %, 0.275 vol %, 0.300 vol %, 0.325 vol %, 0.350 vol %, 0.375 vol %, 0.400 vol %, 0.425 vol %, 0.450 vol %, 0.475 vol %, 0.500 vol %, 0.525 vol %, 0.550 vol %, 0.575 vol %, 0.600 vol %, 0.625 vol %, 0.650 vol %, 0.675 vol %, 0.700 vol %, 0.725 vol %, 0.750 vol %, 0.775 vol %, 0.800 vol %, 0.825 vol %, 0.850 vol %, 0.875 vol %, 0.900 vol %, 0.925 vol %, 0.950 vol %, 0.975 vol %, 1.000 vol %, 1.025 vol %, 1.050 vol %, 1.075 vol %, 1.100 vol %, 1.125 vol %, 1.150 vol %, 1.175 vol %, 1.200 vol %, 1.225 vol %, of 1.250 vol %, 1.275 vol %, 1.300 vol %, 1.325 vol %, 1.350 vol %, 1.375 vol %, 1.400 vol %, 1.425 vol %, 1.450 vol %, 1.475 vol %, 1.500 vol %, 1.525 vol %, 1.550 vol %, 1.575 vol %, 1.600 vol %, 1.625 vol %, 1.650 vol %, 1.675 vol %, 1.700 vol %, 1.725 vol %, 1.750 vol %, 1.775 vol %, 1.800 vol %, 1.825 vol %, 1.850 vol %, 1.875 vol %, 1.900 vol %, 1.925 vol %, 1.950 vol %, 1.975 vol %, 2.000 vol %, 2.025 vol %, 2.050 vol %, 2.075 vol %, 2.100 vol %, 2.125 vol %, 2.150 vol %, 2.175 vol %, 2.200 vol %, 2.225 vol %, of 2.250 vol %, 2.275 vol %, 2.300 vol %, 2.325 vol %, 2.350 vol %, 2.375 vol %, 2.400 vol %, 2.425 vol %, 2.450 vol %, 2.475 vol %, or 2.500 vol % based on a total volume of high-salt cell culture medium.

In some embodiments, the plant oil mixture includes 12.5 to 17.5 wt. % saturated fatty acids based on a total weight of the plant oil mixture. For example, the plant oil mixture can include 12.50 wt. %, 12.75 wt. %, 13.00 wt. %, 13.25 wt. %, 13.50 wt. %, 13.75 wt. %, 14.00 wt. %, 14.25 wt. %, 14.50 wt. %, 14.75 wt. %, 15.00 wt. %, 15.25 wt. %, 15.50 wt. %, 15.75 wt. %, 16.00 wt. %, 16.25 wt. %, 16.50 wt. %, 16.75 wt. %, 17.00 wt. %, 17.25 wt. %, or 17.50 wt. % saturated fatty acids based on a total weight of the plant oil mixture. In some embodiments, the plant oil mixture includes 15.35 wt. % saturated fatty acids based on a total weight of the plant oil mixture.

In some embodiments, the plant oil mixture includes 17.5 to 22.5 wt. %, monounsaturated fatty acids based on a total weight of the plant oil mixture. For example, the plant oil mixture can include 17.50 wt. %, 17.75 wt. %, 18.00 wt. %, 18.25 wt. %, 18.50 wt. %, 18.75 wt. %, 19.00 wt. %, 19.25 wt. %, 19.50 wt. %, 19.75 wt. %, 20.00 wt. %, 20.25 wt. %, 20.50 wt. %, 20.75 wt. %, 21.00 wt. %, 21.25 wt. %, 21.50 wt. %, 21.75 wt. %, 22.00 wt. %, 22.25 wt. %, or 22.50 wt. % monounsaturated fatty acids based on a total weight of the plant oil mixture. In some embodiments, the plant oil mixture includes 20.45 wt. % monounsaturated fatty acids based on a total weight of the plant oil mixture.

In some embodiments, the plant oil mixture includes 25 to 35 wt. % polyunsaturated fatty acids based on a total weight of the plant oil mixture. For example, the plant oil mixture can include 25.00 wt. %, 25.25 wt. %, 25.50 wt. %, 25.75 wt. %, 26.00 wt. %, 26.25 wt. %, 26.75 wt. %, 27.00 wt. %, 27.25 wt. %, 27.50 wt. %, 27.75 wt. %, 28.00 wt. %, 28.25 wt. %, 28.50 wt. %, 28.75 wt. %, 29.00 wt. %, 29.25 wt. %, 29.50 wt. %, 29.75 wt. %, 30.00 wt. %, 30.25 wt. %, 30.50 wt. %, 30.75 wt. %, 31.00 wt. %, 31.25 wt. %, 31.50 wt. %, 31.75 wt. %, 32.00 wt. %, 32.25 wt. %, 32.50 wt. %, 32.75 wt. %, 33.00 wt. %, 33.25 wt. %, 33.50 wt. %, 33.75 wt. %, 34.00 wt. %, 34.25 wt. %, 34.50. wt. %, 34.75 wt. %, or 35.00 wt. % polyunsaturated fatty acids based on a total weight of the plant oil mixture. In some embodiments, the plant oil mixture includes 30.55 wt. % polyunsaturated fatty acids based on the total weight of plant oil mixture.

In some embodiments, the plant oil mixture includes triglycerides. In some embodiments the triglycerides are present as a balance of the weight percentages of the plant oil mixture that is not saturated fatty acids, monounsaturated fatty acids, and polyunsaturated fatty acids.

In some embodiments, the nutrient mixture includes peptone present in an amount of 2 to 4 g per liter (g/L) based on a total volume of the high-salt cell culture medium. For example, the peptone may be present in the high-salt cell culture medium in an amount of 2.0 g/L, 2.25 g/L, 2.5 g/L, 2.75 g/L, 3.0 g/L, 3.25 g/L, 3.5 g/L, 3.75 g/L, or 4.0 g/L. In some embodiments, the nutrient mixture includes 3 g peptone per liter of high-salt cell culture medium.

In some embodiments, the nutrient mixture includes yeast extract present in an amount of 4.0 to 6.0 g per liter (g/L) based on a total volume of the high-salt cell culture medium. For example, the yeast extract may be present in the high-salt cell culture medium in an amount of 4.0 g/L, 4.25 g/L, 4.5 g/L, 4.75 g/L, 5.0 g/L, 5.25 g/L, 5.5 g/L, 5.75 g/L, or 6.0 g/L based on a total volume of the high-salt cell culture medium.

In some embodiments, the high-salt cell culture medium further includes crude oil present in an amount of 0.25 to 2.5 vol. % based on a total volume of high-salt cell culture medium. For example, the crude oil can be present in the high-salt cell culture medium in an amount of 0.250 vol %, 0.255 vol %, 0.260 vol %, 0.265 vol %, 0.270 vol %, 0.275 vol %, 0.280 vol %, 0.285 vol %, 0.290 vol %, 0.295 vol %, 0.300 vol %, 0.305 vol %, 0.310 vol %, 0.315 vol %, 0.320 vol %, 0.325 vol %, 0.330 vol %, 0.335 vol %, 0.340 vol %, 0.345 vol %, 0.350 vol %, 0.355 vol %, 0.360 vol %, 0.365 vol %, 0.370 vol %, 0.375 vol %, 0.380 vol %, 0.385 vol %, 0.390 vol %, 0.395 vol %, 0.400 vol %, 0.405 vol %, 0.410 vol %, 0.415 vol %, 0.420 vol %, 0.425 vol %, 0.430 vol %, 0.435 vol %, 0.440 vol %, 0.445 vol %, 0.450 vol %, 0.455 vol %, 0.460 vol %, 0.465 vol %, 0.470 vol %, 0.475 vol %, 0.480 vol %, 0.485 vol %, 0.490 vol %, 0.495 vol %, 0.500 vol %, 0.505 vol %, 0.510 vol %, 0.515 vol %, 0.520 vol %, 0.525 vol %, 0.530 vol %, 0.535 vol %, 0.540 vol %, 0.545 vol %, 0.550 vol %, 0.555 vol %, 0.560 vol %, 0.565 vol %, 0.570 vol %, 0.575 vol %, 0.580 vol %, 0.585 vol %, 0.590 vol %, 0.595 vol %, 0.600 vol %, 0.605 vol %, 0.610 vol %, 0.615 vol %, 0.620 vol %, 0.625 vol %, 0.630 vol %, 0.635 vol %, 0.640 vol %, 0.645 vol %, 0.650 vol %, 0.655 vol %, 0.660 vol %, 0.665 vol %, 0.670 vol %, 0.675 vol %, 0.680 vol %, 0.685 vol %, 0.690 vol %, 0.695 vol %, 0.700 vol %, 0.705 vol %, 0.710 vol %, 0.715 vol %, 0.720 vol %, 0.725 vol %, 0.730 vol %, 0.735 vol %, 0.740 vol %, 0.745 vol %, 0.750 vol %, 0.755 vol %, 0.760 vol %, 0.765 vol %, 0.770 vol %, 0.775 vol %, 0.780 vol %, 0.785 vol %, 0.790 vol %, 0.795 vol %, 0.800 vol %, 0.805 vol %, 0.810 vol %, 0.815 vol %, 0.820 vol %, 0.825 vol %, 0.830 vol %, 0.835 vol %, 0.840 vol %, 0.845 vol %, 0.850 vol %, 0.855 vol %, 0.860 vol %, 0.865 vol %, 0.870 vol %, 0.875 vol %, 0.880 vol %, 0.885 vol %, 0.890 vol %, 0.895 vol %, 0.900 vol %, 0.905 vol %, 0.910 vol %, 0.915 vol %, 0.920 vol %, 0.925 vol %, 0.930 vol %, 0.935 vol %, 0.940 vol %, 0.945 vol %, 0.950 vol %, 0.955 vol %, 0.960 vol %, 0.965 vol %, 0.970 vol %, 0.975 vol %, 0.980 vol %, 0.985 vol %, 0.990 vol %, 0.995 vol %, 1.000 vol %, 1.005 vol %, 1.010 vol %, 1.015 vol %, 1.020 vol %, 1.025 vol %, 1.030 vol %, 1.035 vol %, 1.040 vol %, 1.045 vol %, 1.050 vol %, 1.055 vol %, 1.060 vol %, 1.065 vol %, 1.070 vol %, 1.075 vol %, 1.080 vol %, 1.085 vol %, 1.090 vol %, 1.095 vol %, 1.100 vol %, 1.105 vol %, 1.110 vol %, 1.115 vol %, 1.120 vol %, 1.125 vol %, 1.130 vol %, 1.135 vol %, 1.140 vol %, 1.145 vol %, 1.150 vol %, 1.155 vol %, 1.160 vol %, 1.165 vol %, 1.170 vol %, 1.175 vol %, 1.180 vol %, 1.185 vol %, 1.190 vol %, 1.195 vol %, 1.200 vol %, 1.205 vol %, 1.210 vol %, 1.215 vol %, 1.220 vol %, 1.225 vol %, 1.230 vol %, 1.235 vol %, 1.240 vol %, 1.245 vol %, 1.250 vol %, 1.255 vol %, 1.260 vol %, 1.265 vol %, 1.270 vol %, 1.275 vol %, 1.280 vol %, 1.285 vol %, 1.290 vol %, 1.295 vol %, 1.300 vol %, 1.305 vol %, 1.310 vol %, 1.315 vol %, 1.320 vol %, 1.325 vol %, 1.330 vol %, 1.335 vol %, 1.340 vol %, 1.345 vol %, 1.350 vol %, 1.355 vol %, 1.360 vol %, 1.365 vol %, 1.370 vol %, 1.375 vol %, 1.380 vol %, 1.385 vol %, 1.390 vol %, 1.395 vol %, 1.400 vol %, 1.405 vol %, 1.410 vol %, 1.415 vol %, 1.420 vol %, 1.425 vol %, 1.430 vol %, 1.435 vol %, 1.440 vol %, 1.445 vol %, 1.450 vol %, 1.455 vol %, 1.460 vol %, 1.465 vol %, 1.470 vol %, 1.475 vol %, 1.480 vol %, 1.485 vol %, 1.490 vol %, 1.495 vol %, 1.500 vol %, 1.505 vol %, 1.510 vol %, 1.515 vol %, 1.520 vol %, 1.525 vol %, 1.530 vol %, 1.535 vol %, 1.540 vol %, 1.545 vol %, 1.550 vol %, 1.555 vol %, 1.560 vol %, 1.565 vol %, 1.570 vol %, 1.575 vol %, 1.580 vol %, 1.585 vol %, 1.590 vol %, 1.595 vol %, 1.600 vol %, 1.605 vol %, 1.610 vol %, 1.615 vol %, 1.620 vol %, 1.625 vol %, 1.630 vol %, 1.635 vol %, 1.640 vol %, 1.645 vol %, 1.650 vol %, 1.655 vol %, 1.660 vol %, 1.665 vol %, 1.670 vol %, 1.675 vol %, 1.680 vol %, 1.685 vol %, 1.690 vol %, 1.695 vol %, 1.700 vol %, 1.705 vol %, 1.710 vol %, 1.715 vol %, 1.720 vol %, 1.725 vol %, 1.730 vol %, 1.735 vol %, 1.740 vol %, 1.745 vol %, 1.750 vol %, 1.755 vol %, 1.760 vol %, 1.765 vol %, 1.770 vol %, 1.775 vol %, 1.780 vol %, 1.785 vol %, 1.790 vol %, 1.795 vol %, 1.800 vol %, 1.805 vol %, 1.810 vol %, 1.815 vol %, 1.820 vol %, 1.825 vol %, 1.830 vol %, 1.835 vol %, 1.840 vol %, 1.845 vol %, 1.850 vol %, 1.855 vol %, 1.860 vol %, 1.865 vol %, 1.870 vol %, 1.875 vol %, 1.880 vol %, 1.885 vol %, 1.890 vol %, 1.895 vol %, 1.900 vol %, 1.905 vol %, 1.910 vol %, 1.915 vol %, 1.920 vol %, 1.925 vol %, 1.930 vol %, 1.935 vol %, 1.940 vol %, 1.945 vol %, 1.950 vol %, 1.955 vol %, 1.960 vol %, 1.965 vol %, 1.970 vol %, 1.975 vol %, 1.980 vol %, 1.985 vol %, 1.990 vol %, 1.995 vol %, 2.000 vol %, 2.005 vol %, 2.010 vol %, 2.015 vol %, 2.020 vol %, 2.025 vol %, 2.030 vol %, 2.035 vol %, 2.040 vol %, 2.045 vol %, 2.050 vol %, 2.055 vol %, 2.060 vol %, 2.065 vol %, 2.070 vol %, 2.075 vol %, 2.080 vol %, 2.085 vol %, 2.090 vol %, 2.095 vol %, 2.100 vol %, 2.105 vol %, 2.110 vol %, 2.115 vol %, 2.120 vol %, 2.125 vol %, 2.130 vol %, 2.135 vol %, 2.140 vol %, 2.145 vol %, 2.150 vol %, 2.155 vol %, 2.160 vol %, 2.165 vol %, 2.170 vol %, 2.175 vol %, 2.180 vol %, 2.185 vol %, 2.190 vol %, 2.195 vol %, 2.200 vol %, 2.205 vol %, 2.210 vol %, 2.215 vol %, 2.220 vol %, 2.225 vol %, 2.230 vol %, 2.235 vol %, 2.240 vol %, 2.245 vol %, 2.250 vol %, 2.255 vol %, 2.260 vol %, 2.265 vol %, 2.270 vol %, 2.275 vol %, 2.280 vol %, 2.285 vol %, 2.290 vol %, 2.295 vol %, 2.300 vol %, 2.305 vol %, 2.310 vol %, 2.315 vol %, 2.320 vol %, 2.325 vol %, 2.330 vol %, 2.335 vol %, 2.340 vol %, 2.345 vol %, 2.350 vol %, 2.355 vol %, 2.360 vol %, 2.365 vol %, 2.370 vol %, 2.375 vol %, 2.380 vol %, 2.385 vol %, 2.390 vol %, 2.395 vol %, 2.400 vol %, 2.405 vol %, 2.410 vol %, 2.415 vol %, 2.420 vol %, 2.425 vol %, 2.430 vol %, 2.435 vol %, 2.440 vol %, 2.445 vol %, 2.450 vol %, 2.455 vol %, 2.460 vol %, 2.465 vol %, 2.470 vol %, 2.475 vol %, 2.480 vol %, 2.485 vol %, 2.490 vol %, 2.495 vol %, or 2.500 vol % based on the total volume of high-salt cell culture medium. the high-salt cell culture medium further includes crude oil present in an amount of 1.00 vol. % based on a total volume of high-salt cell culture medium.

In some embodiments, before the culturing, the high-salt cell culture medium is sterilized. In some embodiments, the high-salt cell culture medium can be sterilized by autoclaving a non-sterile volume of the medium at 115 to 130° C., preferably 118 to 122° C., preferably 121° C. and 5 to 25 psi, preferably 10 to 20 psi, preferably about 15 psi for 10 to 60 minutes, preferably 18 to 22 minutes, preferably 20 minutes.

In general, the culturing may be carried out under aerobic or anaerobic conditions. In some embodiments, the culturing is carried out under anaerobic conditions. In some embodiments, the salt-tolerant bacteria consume petroleum hydrocarbons under oxygen-limited conditions, causing the breakdown/degradation of the petroleum hydrocarbons into smaller products that do not contain additional oxygen atoms. In some embodiments, to produce or ensure anaerobic conditions, the high-salt cell culture medium is deoxygenated. In general, the high-salt cell culture medium can be deoxygenated by any suitable technique known to one of ordinary skill in the art. Examples of such techniques include, but are not limited to, freeze-pump-thaw cycling, bubbling an inert gas such as nitrogen gas through the medium, placing the medium under vacuum, or some combination of these. In some embodiments, the high-salt cell culture medium is deoxygenated by bubbling nitrogen gas through the medium. In some embodiments, the high-salt cell culture medium is substantially free of oxygen. In some embodiments, the salt-tolerant bacteria consume petroleum hydrocarbons under oxygen-rich conditions, causing the breakdown/degradation of the petroleum hydrocarbons into smaller products that contain additional oxygen atoms.

In some embodiments, the salt-tolerant bacteria is cultured at a temperature of 40 to 70° C. For example, the salt-tolerant bacteria can be cultured at a temperature of 40° C., 45° C., 50° C., 55° C., 60° C., 65° C., or 70° C. In some embodiments, the salt-tolerant bacteria is cultured at a temperature of 55° C. In some embodiments, the salt-tolerant bacteria is cultured for 1 to 14 days. For example, the salt-tolerant bacteria may be cultured for 1 day, 2 days, 3 days, 4 days, 5 days, 6 days, 7 days, 8 days, 9 days, 10 days, 11 days, 12 days, 13 days, or 14 days. In some embodiments, the salt-tolerant bacteria is cultured for 7 days. In some embodiments, the salt-tolerant bacteria is cultured under anaerobic conditions.

In some embodiments, following the culturing, the salt-tolerant bacteria is harvested, collected, isolated, or otherwise obtained from the high-salt cell culture medium. In general, the salt-tolerant bacteria can be harvested or collected by any suitable technique, such as suspension and centrifugation, manual colony collection, washing, scraping, and combinations of these. Washing may be performed using a suitable buffer or using the liquid medium described below.

At step 56, the method 50 includes suspending the salt-tolerant bacteria in a liquid medium to form a first broth.

In some embodiments, the liquid medium includes sodium chloride present in an amount of 140 to 160 g per liter (g/L) based on a total volume of liquid medium. For example, the liquid medium can include sodium chloride in an amount of 140.0 g/L, 140.5 g/L, 141.0 g/L, 141.5 g/L, 142.0 g/L, 142.5 g/L, 143.0 g/L, 143.5 g/L, 144.0 g/L, 144.5 g/L, 145.0 g/L, 145.5 g/L, 146.0 g/L, 146.5 g/L, 147.0 g/L, 147.5 g/L, 148.0 g/L, 148.5 g/L, 149.0 g/L, 149.5 g/L, 150.0 g/L, 150.5 g/L, 151.0 g/L, 151.5 g/L, 152.0 g/L, 152.5 g/L, 153.0 g/L, 153.5 g/L, 154.0 g/L, 154.5 g/L, 155.0 g/L, 155.5 g/L, 156.0 g/L, 156.5 g/L, 157.0 g/L, 157.5 g/L, 158.0 g/L, 158.5 g/L, 159.0 g/L, 159.5 g/L, or 160.0 g/L. In some embodiments, the liquid medium includes sodium chloride present in an amount of 150.46 g per liter of liquid medium.

In some embodiments, the liquid medium includes sodium sulfate present in an amount of 0.40 to 0.60 g per liter (g/L) based on a total volume of liquid medium. For example, the liquid medium can include sodium sulfate in an amount of 0.400 g/L, 0.405 g/L, 0.410 g/L, 0.415 g/L, 0.420 g/L, 0.425 g/L, 0.430 g/L, 0.435 g/L, 0.440 g/L, 0.445 g/L, 0.450 g/L, 0.455 g/L, 0.460 g/L, 0.465 g/L, 0.470 g/L, 0.475 g/L, 0.480 g/L, 0.485 g/L, 0.490 g/L, 0.495 g/L, 0.500 g/L, 0.505 g/L, 0.510 g/L, 0.515 g/L, 0.520 g/L, 0.525 g/L, 0.530 g/L, 0.535 g/L, 0.540 g/L, 0.545 g/L, 0.550 g/L, 0.555 g/L, 0.560 g/L, 0.565 g/L, 0.570 g/L, 0.575 g/L, 0.580 g/L, 0.585 g/L, 0.590 g/L, 0.595 g/L, or 0.600 g/L. In some embodiments, the liquid medium includes sodium sulfate present in an amount of 0.5175 g per liter liquid medium.

In some embodiments, the liquid medium includes sodium bicarbonate present in an amount of 0.38 to 0.59 g per liter (g/L) based on a total volume of liquid medium. For example, the liquid medium can include sodium bicarbonate in an amount of 0.380 g/L, 0.385 g/L, 0.390 g/L, 0.395 g/L, 0.400 g/L, 0.405 g/L, 0.410 g/L, 0.415 g/L, 0.420 g/L, 0.425 g/L, 0.430 g/L, 0.435 g/L, 0.440 g/L, 0.445 g/L, 0.450 g/L, 0.455 g/L, 0.460 g/L, 0.465 g/L, 0.470 g/L, 0.475 g/L, 0.480 g/L, 0.485 g/L, 0.490 g/L, 0.495 g/L, 0.500 g/L, 0.505 g/L, 0.510 g/L, 0.515 g/L, 0.520 g/L, 0.525 g/L, 0.530 g/L, 0.535 g/L, 0.540 g/L, 0.545 g/L, 0.550 g/L, 0.555 g/L, 0.560 g/L, 0.565 g/L, 0.570 g/L, 0.575 g/L, 0.580 g/L, 0.585 g/L, or 0.590 g/L. In some embodiments, the liquid medium includes sodium bicarbonate present in an amount of 0.4874 g per liter of liquid medium.

In some embodiments, the liquid medium includes calcium chloride present in an amount of 60 to 80 g per liter (g/L) based on a total volume of liquid medium. For example, the liquid medium can include calcium chloride in an amount of 60.0 g/L, 60.5 g/L, 61.0 g/L, 61.5 g/L, 62.0 g/L, 62.5 g/L, 63.0 g/L, 63.5 g/L, 64.0 g/L, 64.5 g/L, 65.0 g/L, 65.5 g/L, 66.0 g/L, 66.5 g/L, 67.0 g/L, 67.5 g/L, 68.0 g/L, 68.5 g/L, 69.0 g/L, 69.5 g/L, 70.0 g/L, 70.5 g/L, 71.0 g/L, 71.5 g/L, 72.0 g/L, 72.5 g/L, 73.0 g/L, 73.5 g/L, 74.0 g/L, 74.5 g/L, 75.0 g/L, 75.5 g/L, 76.0 g/L, 76.5 g/L, 77.0 g/L, 77.5 g/L, 78.0 g/L, 78.5 g/L, 79.0 g/L, 79.5 g/L, or 80.0 g/L. In some embodiments, the liquid medium includes calcium chloride present in an amount of 69.823 g per liter of liquid medium.

In some embodiments, the liquid medium includes magnesium chloride present in an amount of 10 to 31 g per liter (g/L) based on a total volume of liquid medium. For example, the liquid medium can include magnesium chloride in an amount of 10.0 g/L, 10.5 g/L, 11.0 g/L, 11.5 g/L, 12.0 g/L, 12.5 g/L, 13.0 g/L, 13.5 g/L, 14.0 g/L, 14.5 g/L, 15.0 g/L, 15.5 g/L, 16.0 g/L, 16.5 g/L, 17.0 g/L, 17.5 g/L, 18.0 g/L, 18.5 g/L, 19.0 g/L, 19.5 g/L, 20.0 g/L, 20.5 g/L, 21.0 g/L, 21.5 g/L, 22.0 g/L, 22.5 g/L, 23.0 g/L, 23.5 g/L, 24.0 g/L, 24.5 g/L, 25.0 g/L, 25.5 g/L, 26.0 g/L, 26.5 g/L, 27.0 g/L, 27.5 g/L, 28.0 g/L, 28.5 g/L, 29.0 g/L, 29.5 g/L, 30.0 g/L, 30.5 g/L, or 31.0 g/L. In some embodiments, the liquid medium includes magnesium chloride present in an amount of 20.395 g per liter of liquid culture medium.

In some embodiments, the liquid medium includes glycerol present in an amount of 1 to 5 vol %, based on a total volume of liquid medium. For example, the liquid medium can include glycerol in an amount of 1.0 wt. %, 1.25 wt. %, 1.5 wt. %, 1.75 wt. %, 2.0 wt. %, 2.25 wt. %, 2.5 wt. %, 2.75 wt. %, 3.0 wt. %, 3.25 wt. %, 3.5 wt. %, 3.75 wt. %, 4.0 wt. %, 4.25 wt. %, 4.5 wt. %, 4.75 wt. %, or 5.0 wt. %, based on a total volume of liquid culture medium.

In some embodiments, the liquid medium does not include a solidifying or gelling agent such as agar. In some embodiments, the liquid medium includes water. As implied by the name "liquid medium", the liquid medium is preferably a liquid.

In some embodiments, the liquid medium further includes a nutrient supplement that is at least one selected from the group consisting of a plant oil mixture and a nutrient mixture.

In some embodiments, the plant oil mixture is present in an amount of 0.25 to 2.5 vol % based on the total volume of the liquid medium. For example, the plant oil mixture may be present in an amount of 0.250 vol %, 0.275 vol %, 0.300 vol %, 0.325 vol %, 0.350 vol %, 0.375 vol %, 0.400 vol %, 0.425 vol %, 0.450 vol %, 0.475 vol %, 0.500 vol %, 0.525 vol %, 0.550 vol %, 0.575 vol %, 0.600 vol %, 0.625 vol %, 0.650 vol %, 0.675 vol %, 0.700 vol %, 0.725 vol %, 0.750 vol %, 0.775 vol %, 0.800 vol %, 0.825 vol %, 0.850 vol %, 0.875 vol %, 0.900 vol %, 0.925 vol %, 0.950 vol %, 0.975 vol %, 1.000 vol %, 1.025 vol %, 1.050 vol %, 1.075 vol %, 1.100 vol %, 1.125 vol %, 1.150 vol %, 1.175 vol %, 1.200 vol %, 1.225 vol %, of 1.250 vol %, 1.275 vol %, 1.300 vol %, 1.325 vol %, 1.350 vol %, 1.375 vol %, 1.400 vol %, 1.425 vol %, 1.450 vol %, 1.475 vol %, 1.500 vol %, 1.525 vol %, 1.550 vol %, 1.575 vol %, 1.600 vol %, 1.625 vol %, 1.650 vol %, 1.675 vol %, 1.700 vol %, 1.725 vol %, 1.750 vol %, 1.775 vol %, 1.800 vol %, 1.825 vol %, 1.850 vol %, 1.875 vol %, 1.900 vol %, 1.925 vol %, 1.950 vol %, 1.975 vol %, 2.000 vol %, 2.025 vol %, 2.050 vol %, 2.075 vol %, 2.100 vol %, 2.125 vol %, 2.150 vol %, 2.175 vol %, 2.200 vol %, 2.225 vol %, of 2.250 vol %, 2.275 vol %, 2.300 vol %, 2.325 vol %, 2.350 vol %, 2.375 vol %, 2.400 vol %, 2.425 vol %, 2.450 vol %, 2.475 vol %, or 2.500 vol % based on a total volume of liquid culture medium.

In some embodiments, the plant oil mixture includes 12.5 to 17.5 wt. % saturated fatty acids based on a total weight of the plant oil mixture. For example, the plant oil mixture can include 12.50 wt. %, 12.75 wt. %, 13.00 wt. %, 13.25 wt. %, 13.50 wt. %, 13.75 wt. %, 14.00 wt. %, 14.25 wt. %, 14.50 wt. %, 14.75 wt. %, 15.00 wt. %, 15.25 wt. %, 15.50 wt. %, 15.75 wt. %, 16.00 wt. %, 16.25 wt. %, 16.50 wt. %, 16.75 wt. %, 17.00 wt. %, 17.25 wt. %, or 17.50 wt. % saturated fatty acids based on a total weight of the plant oil mixture. In some embodiments, the plant oil mixture includes 15.35 wt. % saturated fatty acids based on a total weight of the plant oil mixture.

In some embodiments, the plant oil mixture includes 17.5 to 22.5 wt. %, monounsaturated fatty acids based on a total weight of the plant oil mixture. For example, the plant oil mixture can include 17.50 wt. %, 17.75 wt. %, 18.00 wt. %, 18.25 wt. %, 18.50 wt. %, 18.75 wt. %, 19.00 wt. %, 19.25 wt. %, 19.50 wt. %, 19.75 wt. %, 20.00 wt. %, 20.25 wt. %, 20.50 wt. %, 20.75 wt. %, 21.00 wt. %, 21.25 wt. %, 21.50 wt. %, 21.75 wt. %, 22.00 wt. %, 22.25 wt. %, or 22.50 wt. % monounsaturated fatty acids based on a total weight of the plant oil mixture. In some embodiments, the plant oil mixture includes 20.45 wt. % monounsaturated fatty acids based on a total weight of the plant oil mixture.

In some embodiments, the plant oil mixture includes 25 to 35 wt. % polyunsaturated fatty acids based on a total weight of the plant oil mixture. For example, the plant oil mixture can include 25.00 wt. %, 25.25 wt. %, 25.50 wt. %, 25.75 wt. %, 26.00 wt. %, 26.25 wt. %, 26.75 wt. %, 27.00 wt. %, 27.25 wt. %, 27.50 wt. %, 27.75 wt. %, 28.00 wt. %, 28.25 wt. %, 28.50 wt. %, 28.75 wt. %, 29.00 wt. %, 29.25 wt. %, 29.50 wt. %, 29.75 wt. %, 30.00 wt. %, 30.25 wt. %, 30.50 wt. %, 30.75 wt. %, 31.00 wt. %, 31.25 wt. %, 31.50 wt. %, 31.75 wt. %, 32.00 wt. %, 32.25 wt. %, 32.50 wt. %, 32.75 wt. %, 33.00 wt. %, 33.25 wt. %, 33.50 wt. %, 33.75 wt. %, 34.00 wt. %, 34.25 wt. %, 34.50. wt. %, 34.75 wt. %, or 35.00 wt. % polyunsaturated fatty acids based on a total weight of the plant oil mixture. In some embodiments, the plant oil mixture includes 30.55 wt. % polyunsaturated fatty acids based on the total weight of plant oil mixture.

In some embodiments, the plant oil mixture includes triglycerides. In some embodiments the triglycerides are present as a balance of the weight percentages of the plant oil mixture that is not saturated fatty acids, monounsaturated fatty acids, and polyunsaturated fatty acids.

In some embodiments, the nutrient mixture includes peptone present in an amount of 2 to 4 g per liter (g/L) based on a total volume of the liquid medium. For example, the peptone may be present in the liquid medium in an amount of 2.0 g/L, 2.25 g/L, 2.5 g/L, 2.75 g/L, 3.0 g/L, 3.25 g/L, 3.5 g/L, 3.75 g/L, or 4.0 g/L. In some embodiments, the nutrient mixture includes 3 g peptone per liter of liquid medium.

In some embodiments, the nutrient mixture includes yeast extract present in an amount of 4.0 to 6.0 g per liter (g/L) based on a total volume of the liquid medium. For example, the yeast extract may be present in the liquid in an amount of 4.0 g/L, 4.25 g/L, 4.5 g/L, 4.75 g/L, 5.0 g/L, 5.25 g/L, 5.5 g/L, 5.75 g/L, or 6.0 g/L based on a total volume of the liquid medium.

In some embodiments, the liquid medium further includes crude oil present in an amount of 1 to 40 vol. %, based on the total volume of the liquid medium. For example, the crude oil may be present in the liquid medium in an amount of 1.0 vol %, 1.5 vol %, 2.0 vol %, 2.5 vol %, 3.0 vol %, 3.5 vol %, 4.0 vol %, 4.5 vol %, 5.0 vol %, 5.5 vol %, 6.0 vol %, 6.5 vol %, 7.0 vol %, 7.5 vol %, 8.0 vol %, 8.5 vol %, 9.0 vol %, 9.5 vol %, 10.0 vol %, 10.5 vol %, 11.0 vol %, 11.5 vol %, 12.0 vol %, 12.5 vol %, 13.0 vol %, 13.5 vol %, 14.0 vol %, 14.5 vol %, 15.0 vol %, 15.5 vol %, 16.0 vol %, 16.5 vol %, 17.0 vol %, 17.5 vol %, 18.0 vol %, 18.5 vol %, 19.0 vol %, 19.5 vol %, 20.0 vol %, 20.5 vol %, 21.0 vol %, 21.5 vol %, 22.0 vol %, 22.5 vol %, 23.0 vol %, 23.5 vol %, 24.0 vol %, 24.5 vol %, 25.0 vol %, 25.5 vol %, 26.0 vol %, 26.5 vol %, 27.0 vol %, 27.5 vol %, 28.0 vol %, 28.5 vol %, 29.0 vol %, 29.5 vol %, 30.0 vol %, 30.5 vol %, 31.0 vol %, 31.5 vol %, 32.0 vol %, 32.5 vol %, 33.0 vol %, 33.5 vol %, 34.0 vol %, 34.5 vol %, 35.0 vol %, 35.5 vol %, 36.0 vol %, 36.5 vol %, 37.0 vol %, 37.5 vol %, 38.0 vol %, 38.5 vol %, 39.0 vol %, 39.5 vol %, or 40 vol %. In some embodiments, the amount of crude oil present in the liquid medium may be altered in successive rounds of incubation as described below.

In some embodiments, the liquid medium is deoxygenated. In general, the liquid medium may be deoxygenated as described above. In some embodiments, the liquid medium is deoxygenated by bubbling nitrogen gas through the liquid medium. In some embodiments, the liquid medium is substantially free of oxygen.

In some embodiments, the liquid medium is sterilized. In general, the liquid medium may be sterilized as described above. In some embodiments, the liquid medium is sterilized by autoclaving a non-sterile volume of the liquid medium at 115 to 130° C., preferably 118 to 122° C., preferably 121° C. and 5 to 25 psi, preferably 10 to 20 psi, preferably about 15 psi for 10 to 60 minutes, preferably 18 to 22 minutes, preferably 20 minutes.

At step 58, the method 50 includes incubating the first broth to form an inoculation mixture. In some embodiment, the first broth is incubated at a temperature of 40 to 75° C. For example, the salt-tolerant bacteria can be cultured at a temperature of 40° C., 45° C., 50° C., 55° C., 60° C., 65° C., 70° C., or 75° C. In some embodiments, the first broth is incubated at a temperature of 55° C. In some embodiments, the first broth is incubated for 30 to 120 days. For example, the first broth may be incubated for 30 days, 35 days, 40 days, 45 days, 50 days, 55 days, 60 days, 65 days, 70 days, 75 days, 80 days, 85 days, 90 days, 95 days, 100 days, 105 days, 110 days, 115 days, or 120 days. In some embodiments, the first broth is incubated for 90 days. In some embodiments, the incubation is performed under anaerobic conditions.

In some embodiments, following the incubating, the salt-tolerant bacteria is harvested, collected, isolated, or otherwise obtained from the liquid medium. In general, the salt-tolerant bacteria can be harvested or collected by any suitable technique, such as centrifugation, filtering, and the like.

In some embodiments, the collected or isolated salt-tolerant bacteria may be resuspended in the liquid medium for further incubation. A process of resuspension, incubation, and collection/harvesting may be referred to as a "round", "cycle", or other similar term. In some embodiments, the collected or isolated salt-tolerant bacteria is resuspended in a liquid medium having a higher amount of crude oil than the liquid medium used in the previous round or cycle.

In some embodiments, the collected or isolated salt-tolerant bacteria may be dried, frozen, freeze-dried, or otherwise prepared for storage. Such storage may include the liquid medium. Preferably, the storage is performed under conditions (moisture level, pH, temperature, nutrients, etc.) appropriate to maintain a sufficient microbial/bacterial population conducive to bioremediation.

At step 60, the method 50 includes mixing the inoculation mixture with production water in a volume ratio of 1:1 to form a bacteria-containing liquid mixture.

At step 62, the method 50 includes bioremediating the treated production water by propagating the inoculation liquid mixture in the treated production water. In some embodiments, the treated production water is deoxygenated prior to the propagating the inoculation mixture. In general, the deoxygenating can be performed as described above, for example by bubbling nitrogen gas through the treated production water. In some embodiments, the bacteria-containing liquid mixture is substantially free of oxygen.

In some embodiments, the method includes adding a nutrient supplement to the treated production water which is at least one selected from a plant oil mixture and a nutrient mixture. In some embodiments, the plant oil mixture is present in an amount of 0.25 to 2.5 vol % based on the total volume of the bacteria-containing liquid mixture. For example, the plant oil mixture may be present in an amount of 0.250 vol %, 0.275 vol %, 0.300 vol %, 0.325 vol %, 0.350 vol %, 0.375 vol %, 0.400 vol %, 0.425 vol %, 0.450 vol %, 0.475 vol %, 0.500 vol %, 0.525 vol %, 0.550 vol %, 0.575 vol %, 0.600 vol %, 0.625 vol %, 0.650 vol %, 0.675 vol %, 0.700 vol %, 0.725 vol %, 0.750 vol %, 0.775 vol %, 0.800 vol %, 0.825 vol %, 0.850 vol %, 0.875 vol %, 0.900 vol %, 0.925 vol %, 0.950 vol %, 0.975 vol %, 1.000 vol %, 1.025 vol %, 1.050 vol %, 1.075 vol %, 1.100 vol %, 1.125 vol %, 1.150 vol %, 1.175 vol %, 1.200 vol %, 1.225 vol %, of 1.250 vol %, 1.275 vol %, 1.300 vol %, 1.325 vol %, 1.350 vol %, 1.375 vol %, 1.400 vol %, 1.425 vol %, 1.450 vol %, 1.475 vol %, 1.500 vol %, 1.525 vol %, 1.550 vol %, 1.575 vol %, 1.600 vol %, 1.625 vol %, 1.650 vol %, 1.675 vol %, 1.700 vol %, 1.725 vol %, 1.750 vol %, 1.775 vol %, 1.800 vol %, 1.825 vol %, 1.850 vol %, 1.875 vol %, 1.900 vol %, 1.925 vol %, 1.950 vol %, 1.975 vol %, 2.000 vol %, 2.025 vol %, 2.050 vol %, 2.075 vol %, 2.100 vol %, 2.125 vol %, 2.150 vol %, 2.175 vol %, 2.200 vol %, 2.225 vol %, of 2.250 vol %, 2.275 vol %, 2.300 vol %, 2.325 vol %, 2.350 vol %, 2.375 vol %, 2.400 vol %, 2.425 vol %, 2.450 vol %, 2.475 vol %, or 2.500 vol % based on a total volume of bacteria-containing liquid mixture.

In some embodiments, the plant oil mixture includes 12.5 to 17.5 wt. % saturated fatty acids based on a total weight of the plant oil mixture. For example, the plant oil mixture can include 12.50 wt. %, 12.75 wt. %, 13.00 wt. %, 13.25 wt. %, 13.50 wt. %, 13.75 wt. %, 14.00 wt. %, 14.25 wt. %, 14.50 wt. %, 14.75 wt. %, 15.00 wt. %, 15.25 wt. %, 15.50 wt. %, 15.75 wt. %, 16.00 wt. %, 16.25 wt. %, 16.50 wt. %, 16.75 wt. %, 17.00 wt. %, 17.25 wt. %, or 17.50 wt. % saturated fatty acids based on a total weight of the plant oil mixture. In some embodiments, the plant oil mixture includes 15.35 wt. % saturated fatty acids based on a total weight of the plant oil mixture.

In some embodiments, the plant oil mixture includes 17.5 to 22.5 wt. %, monounsaturated fatty acids based on a total weight of the plant oil mixture. For example, the plant oil mixture can include 17.50 wt. %, 17.75 wt. %, 18.00 wt. %, 18.25 wt. %, 18.50 wt. %, 18.75 wt. %, 19.00 wt. %, 19.25 wt. %, 19.50 wt. %, 19.75 wt. %, 20.00 wt. %, 20.25 wt. %, 20.50 wt. %, 20.75 wt. %, 21.00 wt. %, 21.25 wt. %, 21.50 wt. %, 21.75 wt. %, 22.00 wt. %, 22.25 wt. %, or 22.50 wt. % monounsaturated fatty acids based on a total weight of the plant oil mixture. In some embodiments, the plant oil mixture includes 20.45 wt. % monounsaturated fatty acids based on a total weight of the plant oil mixture.

In some embodiments, the plant oil mixture includes 25 to 35 wt. % polyunsaturated fatty acids based on a total weight of the plant oil mixture. For example, the plant oil mixture can include 25.00 wt. %, 25.25 wt. %, 25.50 wt. %, 25.75 wt. %, 26.00 wt. %, 26.25 wt. %, 26.75 wt. %, 27.00 wt. %, 27.25 wt. %, 27.50 wt. %, 27.75 wt. %, 28.00 wt. %, 28.25 wt. %, 28.50 wt. %, 28.75 wt. %, 29.00 wt. %, 29.25 wt. %, 29.50 wt. %, 29.75 wt. %, 30.00 wt. %, 30.25 wt. %, 30.50 wt. %, 30.75 wt. %, 31.00 wt. %, 31.25 wt. %, 31.50 wt. %, 31.75 wt. %, 32.00 wt. %, 32.25 wt. %, 32.50 wt. %, 32.75 wt. %, 33.00 wt. %, 33.25 wt. %, 33.50 wt. %, 33.75 wt. %, 34.00 wt. %, 34.25 wt. %, 34.50. wt. %, 34.75 wt. %, or 35.00 wt. % polyunsaturated fatty acids based on a total weight of the plant oil mixture. In some embodiments, the plant oil mixture includes 30.55 wt. % polyunsaturated fatty acids based on the total weight of plant oil mixture.

In some embodiments, the plant oil mixture includes triglycerides. In some embodiments the triglycerides are present as a balance of the weight percentages of the plant oil mixture that is not saturated fatty acids, monounsaturated fatty acids, and polyunsaturated fatty acids.

In some embodiments, the nutrient mixture includes peptone present in an amount of 2 to 4 g per liter (g/L) based on a total volume of the bacteria-containing liquid mixture. For example, the peptone may be present in the bacteria-containing liquid mixture in an amount of 2.0 g/L, 2.25 g/L, 2.5 g/L, 2.75 g/L, 3.0 g/L, 3.25 g/L, 3.5 g/L, 3.75 g/L, or 4.0 g/L. In some embodiments, the nutrient mixture includes 3 g peptone per liter of bacteria-containing liquid mixture.

In some embodiments, the nutrient mixture includes yeast extract present in an amount of 4.0 to 6.0 g per liter (g/L) based on a total volume of the bacteria-containing liquid mixture. For example, the yeast extract may be present in the bacteria-containing liquid mixture in an amount of 4.0 g/L, 4.25 g/L, 4.5 g/L, 4.75 g/L, 5.0 g/L, 5.25 g/L, 5.5 g/L, 5.75 g/L, or 6.0 g/L based on a total volume of the bacteria-containing liquid mixture.

In some embodiments, the bioremediating includes mixing the treated production water and the bacteria-containing liquid mixture and circulating in a holding tank having an open top exposed to sunlight with a residence time of 2-3 days.

In general, the method of the present disclosure can be performed in any suitable production water located in any suitable environment. For example, the production water can be an environmental production water that is present in a natural environment such as located in or associated with a soil, sediment, aquifer, groundwater, river, stream, lake, pond, marsh, estuary, ocean, and the like. The production water can be located in or associated with a non-natural (e.g., man-made) environment or facility. For example, the production water can be located in or associated with an oil well, a geothermal well, a mine, a petroleum refinery, a natural gas well, a hydraulic fracturing facility, a hydraulic fracturing liquid treatment facility, and the like.

In some embodiments, following the introduction of the bacteria-containing liquid mixture, the production water can be agitated. Such agitation may be advantageous to ensure adequate mixing of various components of the production water and bacteria-containing liquid mixture. Such agitation can be performed by any suitable method. For example, the agitation can be performed by mechanical stirring. The agitation can also be performed by introducing a gas into the production water, such as by pumping. The gas may be introduced below the surface of the production water to produce bubbles or agitation as the gas rises and/or escapes from the production water. Such gas introduction may be advantageous for introducing oxygen into the production water and/or bacteria-containing liquid mixture in embodiments where the method is performed under aerobic conditions.

In some embodiments, the method of the present disclosure may be used for or as part of bioremediation of a hydrocarbon contaminated site. Contaminated sites may include one or more petroleum or natural gas production areas, landfills, dumps, waste storage and treatment sites, mine tailings sites, spill sites, and chemical waste handler and storage sites.

In some embodiments, the bioremediating involves emulsification. As used herein, emulsification refers to a process by which an emulsion is formed. As used herein, an "emulsion" is a mixture of at least two immiscible liquids where one liquid (e.g., oil, hydrocarbons) is dispersed (e.g., in the form of droplets) within another liquid (e.g., water). Emulsions in which oil or water-insoluble hydrocarbons are dispersed in water are commonly known as oil-in-water emulsions. Emulsification can occur when a suitable chemical agent is added to a mixture of the two immiscible liquids. Such chemical agents are referred to as emulsifiers. Commonly, surfactants are used as emulsifiers. In some embodiments, the bioremediating involves demulsification. Demulsification refers to a process by which an emulsion is destroyed. That is, the emulsion is separated into two separate liquid phases. Demulsification can occur when a suitable chemical agent is added to an emulsion. Some chemical agents can act as both emulsifiers and demulsifiers depending on various factors such as concentration, temperature, the identity of the liquids present in the emulsion, salt concentration, and the like. Emulsifiers and/or demulsifiers (also known as emulsion breakers) may be present in production water.

In some embodiments, the emulsification or demulsification involves chemical action of a chemical agent produced by the salt-tolerant bacteria. Such a chemical agent can be referred to as a "bio-emulsifier" or "biosurfactant". In some embodiments, the salt-tolerant bacteria is selected based on a ability to produce a suitable biosurfactant. Examples of biosurfactants include glycolipids such as rhamnolipid and trehalolipids, lipopeptides, phospholipids, and polymeric biosurfactants such as emulsan and liposan.

In some embodiments, the formation or destruction of an emulsion can enhance the bioremediation. For example, the formation or destruction of an emulsion can facilitate mechanical removal of the hydrocarbons, chemical separation of the hydrocarbons, and/or biodegradation of the hydrocarbons.

In some embodiments, the method of the present disclosure may be adapted for or used in a method of oil biorefining. In some embodiments, the method of the present disclosure may be adapted for or used in a method of enhanced oil recovery. In some embodiments, the method of the present disclosure may be adapted for or used in a method of biodegrading hydrocarbons in an oil-contaminated environment. In some embodiments, the method includes introducing a consortium of bacteria into the environment, wherein the bacteria are selected based on their ability to degrade hydrocarbons under high salinity conditions, providing a nutrient-rich medium optimized for the growth and metabolic activities of the bacterial consortium, and continuously agitating the medium and maintaining specific environmental conditions to maximize the biodegradation rate of hydrocarbons.

In some embodiments, the method of the present disclosure may be adapted to enhance the yield of valuable hydrocarbons during oil refining. In some embodiments, the method includes utilizing microorganisms with specific metabolic pathways that target and convert less valuable hydrocarbons into more valuable ones. In some embodiments, the method includes implementing a bioreactor system designed to support the growth and metabolic activity of these microorganisms. In some embodiments, the method includes optimizing the bioreactor operating conditions, including nutrient supply, aeration, and temperature, to maximize the conversion of hydrocarbons.

In some embodiments, the method of the present disclosure may be adapted for or used in a method of increasing the microbial diversity in an oil-contaminated environment. Such an increase in microbial diversity may be useful for enhancing bioremediation and/or oil recovery. In some embodiments, the method includes cultivating a microbial consortium in a medium designed to mimic the chemical composition of the contaminated site. In some embodiments, the method includes utilizing a controlled enrichment process under specific anaerobic conditions with the addition of nitrogen gas to promote the growth of diverse microbial species. In some embodiments, the method include analyzing the diversity of the enriched microbial population, for example, through alpha diversity measures and rarefaction curves to ensure a robust consortium.

In some embodiments, the method of the present disclosure may be adapted for or used in a method of formulating a microbial additive for oil recovery. In some embodiments, the method includes selecting a combination of microbial strains based on diversity data indicative of efficient oil biodegradation and emulsification capability. In some embodiments, the method includes producing a microbial additive in a form suitable for injection into oil reservoirs. Such a microbial additive may be formulated for one or more purposes, including stabilization and preservation of microbial viability. In some embodiments, the method includes injecting the microbial additive into an oil reservoir to enhance oil recovery through in situ biodegradation and emulsification of oil constituents.

In some embodiments, the method of the present disclosure may be adapted for or used in a method of biocatalytic conversion of heavy oils into lighter fractions. In some embodiments, the method includes identifying enzymes produced by microorganisms that catalyze the cracking of long-chain hydrocarbons. In some embodiments, the method includes incorporating these enzymes into a catalytic reactor system designed for the processing of heavy oils. In some embodiments, the method includes adjusting the reactor conditions to optimize the enzymatic cracking process. The method may increase the yield of lighter, more valuable hydrocarbon fractions.

In some embodiments, the method of present disclosure may be adapted for or used in a method of converting heavy oil into lighter fractions via microbial activity. In some embodiments, the method includes identifying microorganisms capable of hydrocarbon cracking, such as certain species of *Halomonas* and *Bacillus*. In some embodiments, the method includes cultivating these organisms under conditions that stimulate the production of hydrocarbon-cracking enzymes. These microorganisms or their enzymes are introduced into heavy oil fractions to facilitate the conversion into lighter, more valuable products.

In some embodiments, the method of the present disclosure may be adapted to or used in a method to increase the octane rating of gasoline using microbial consortia. In some embodiments, the method includes formulating a microbial consortium capable of isomerizing n-alkanes to branched alkanes, cultivating the microbial consortium in conditions that maximize the isomerization activity, and processing a gasoline fraction through the microbial culture to increase its octane rating and quality.

In some embodiments, the method of the present disclosure may be adapted for or used in a method of bioaugmentation in oil reservoirs using specific microbial strains. The method includes selecting microbial strains from the genus *Halomonas* for their ability to tolerate high salinity and contribute to hydrocarbon degradation, cultivating selected strains and introducing them into oil reservoirs to enhance crude oil emulsification and saponification, and monitoring the performance of introduced strains in increasing the availability and recovery of oil in the reservoir.

In some embodiments, the method of the present disclosure may be adapted for microbial-enhanced oil recovery (MEOR) using targeted bacterial strains. The method includes selecting bacterial strains based on their abundance in samples from oil-producing environments, such as *Halomonas* and *Bacillus* species, and injecting these strains into oil wells to modify the viscosity and surface tension of the oil.

In some embodiments, the method of the present disclosure may be adapted to enhance crude oil quality during the refining process. The method includes utilizing microbial strains from Halmonas and *Bacillus* due to their high abundance and hydrocarbon affinity and propagating the microbial strains into the crude oil to promote biocatalytic reactions that improve oil quality.

EXAMPLES

The following examples demonstrate a method of bioremediating a hydrocarbon-contaminated production water. The examples also demonstrate certain aspects of a method of microbially enhanced oil recovery. The examples are provided solely for illustration and are not to be construed as limitations of the present disclosure, as many variations thereof are possible without departing from the spirit and scope of the present disclosure.

Figure 2:
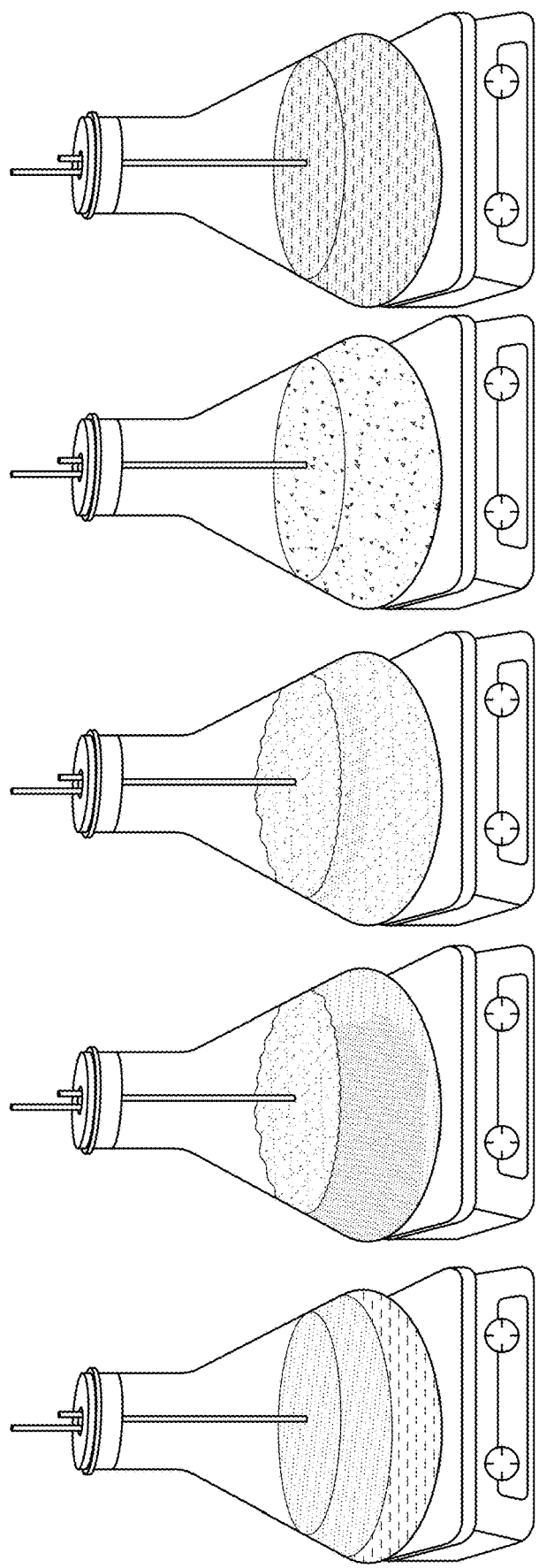
FIG. 2 shows the growth of enrichment culture media, expressed in terms of its turbidity at different incubation periods, according to certain embodiments.

Example 1: Culture Media Preparation Method, Enrichment, and Isolation Procedure The enrichment culture medium was prepared using synthetic formation brine solution, NaCl concentration of 2.574603 mol/L. The formation brine solution was prepared by adding 150.46 g of NaCl, 0.5175 g of $Na_2SO_4$, 0.4784 f of $NaHCO_3$, 69.823 g of $CaCl_2$) dihydrate, 20.395 g of $MgCl_2$ $6.H_2O$, 1 g of $KH_2PO_4$, 1 g $K_2HPO_4$, 1 g $NH_2NO_3$, 0.2 g $MgSO_4$, 0.05 g $FeCl_2$, 3% v/v glycerol, 2% w/v stearic acid, 2% w/v palmitic acid, 1% v/v hexadecane, and 758.32 ml of distilled water. The solution was stirred until the added materials were dissolved entirely, and 25% (vol/vol) commercial plant oils (fatty acids) like triacylglycerols (also known as triglycerides), phospholipids, and sterols (total fat, 100g; saturated fat, 15.35 g; monosaturated fat, 20.45 g; polyunsaturated fat 30.55 g; trans-fat, 0.5 g per 100 mL. The pH of the resulting solution was adjusted to 7.2 by adding 1 N NaOH; the salinity of the medium was 3000 ppt. The medium was sterilized by autoclaving at 121° C. for 20 minutes and then brought down to room temperature. After reaching room temperature, the crude oil was added at 25% vol/vol. The medium was assessed by using a borosilicate glass, flat bottom, Erlenmeyer flask (2500 mL) with a working volume of 2000 mL and continuously stirred at 200 rpm using a magnetic stirrer with 55° C. and deoxygenated by bubbling nitrogen gas (99.9999%). The anaerobic condition of the culture medium was maintained, and the flasks were sealed with rubber stoppers with adhesive tape in continuous mode for more than 90 days. FIG. 2 shows the growth of enrichment culture media, expressed in terms of its turbidity at different incubation periods.

Figure 3:
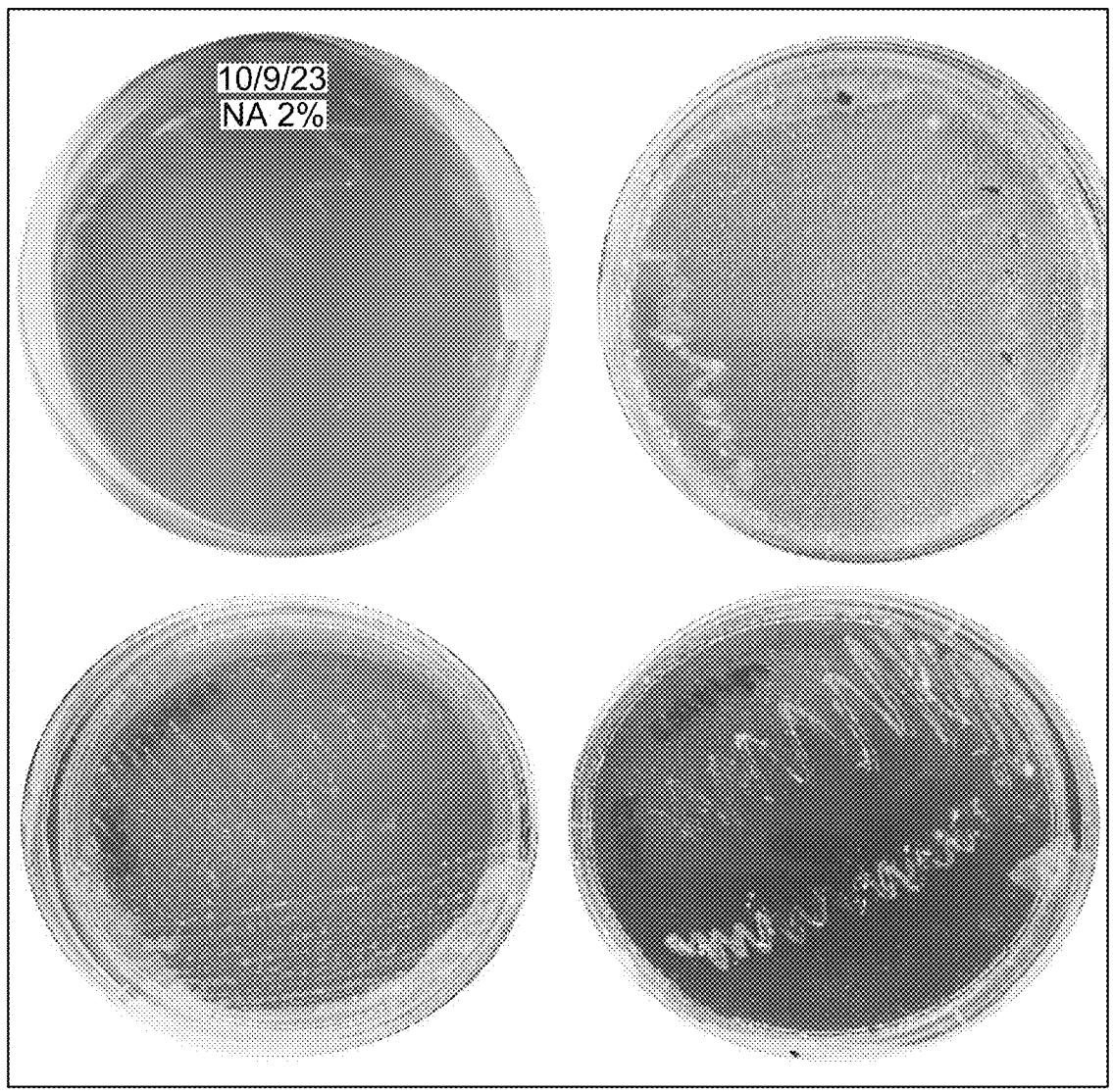
FIG. 3 is a pictorial image of bacterial colonies grown on *Fusobacterium* Selective Agar (FBFA) media, according to certain embodiments.
Figure 4:
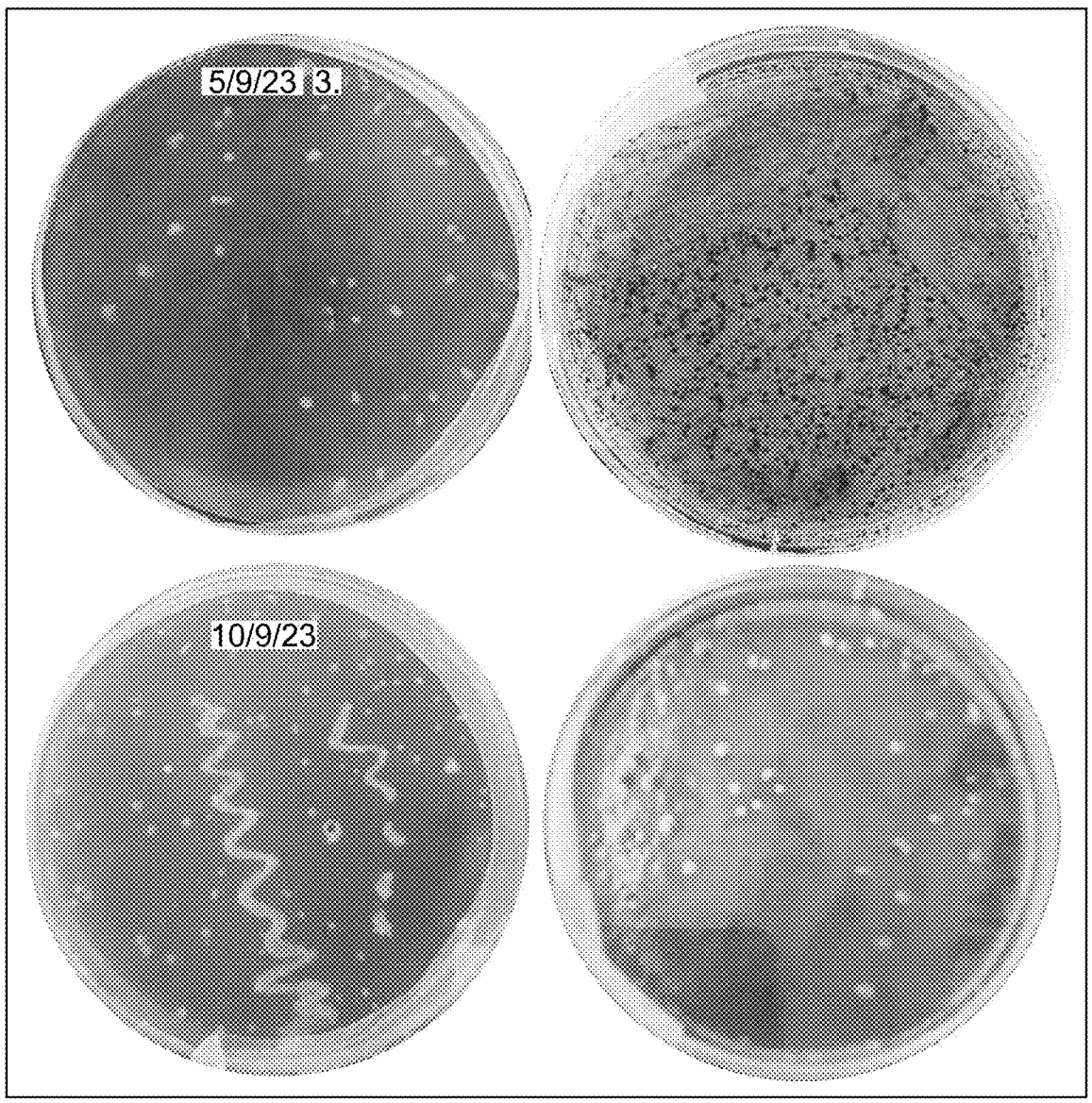
FIG. 4 is a pictorial image of bacterial colonies grown on FBCU agar media, according to certain embodiments.
Figure 5:
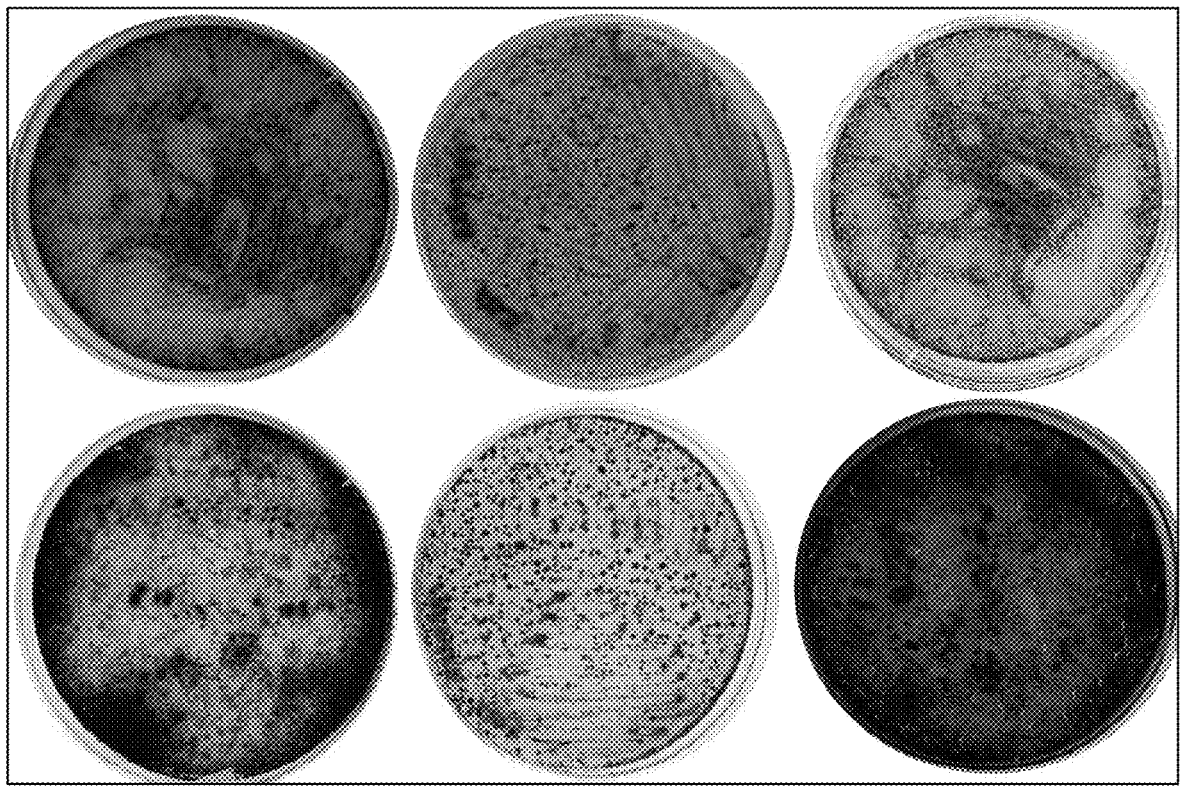
FIG. 5 is a pictorial image of bacterial colonies grown on FBFACU agar media, according to certain embodiments.
Figure 6:
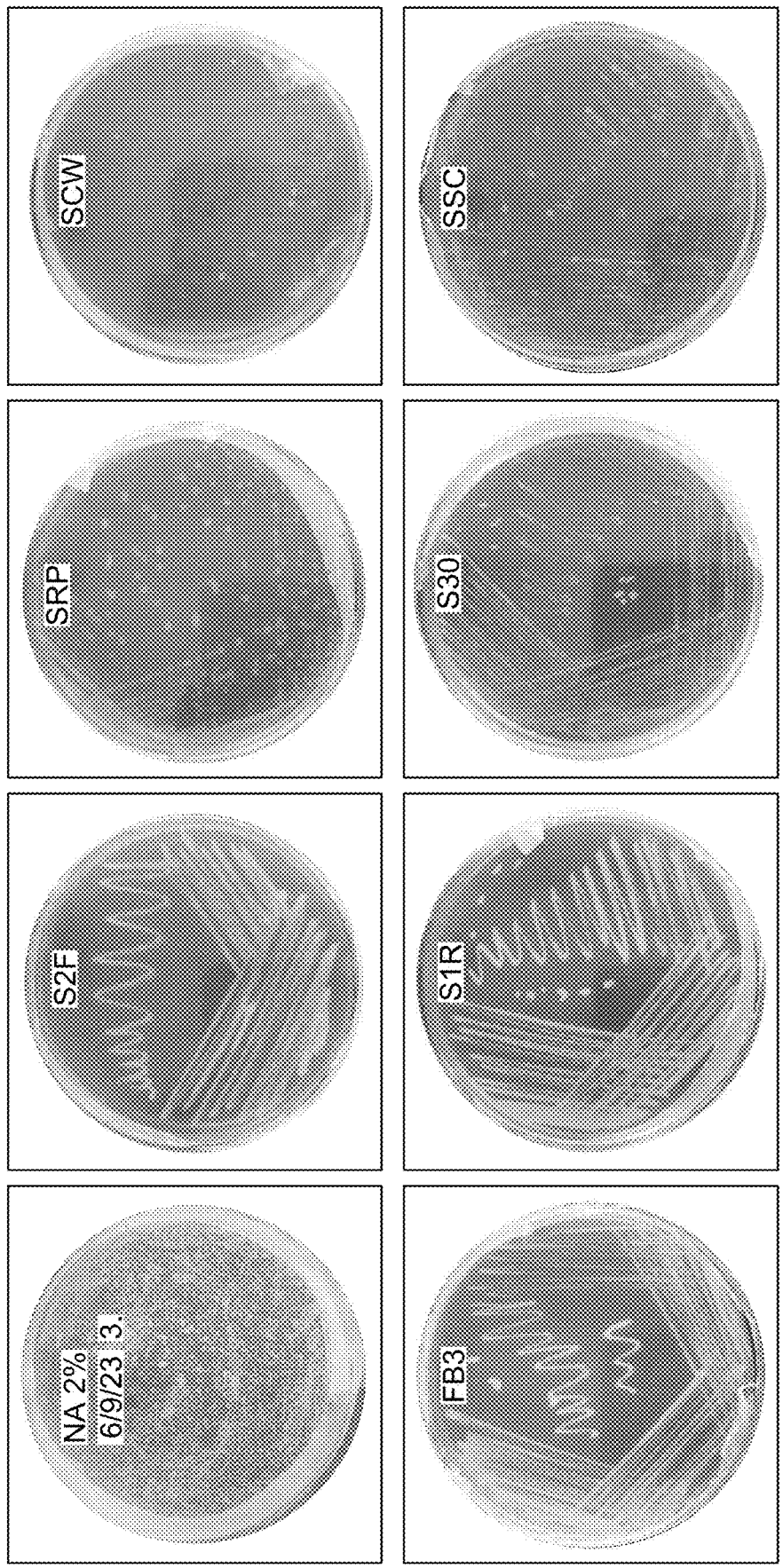
FIG. 6 is a pictorial image of the isolated pure bacterial strains grown in bacterial colonies in FBNB agar media, according to certain embodiments.
Figure 7A:
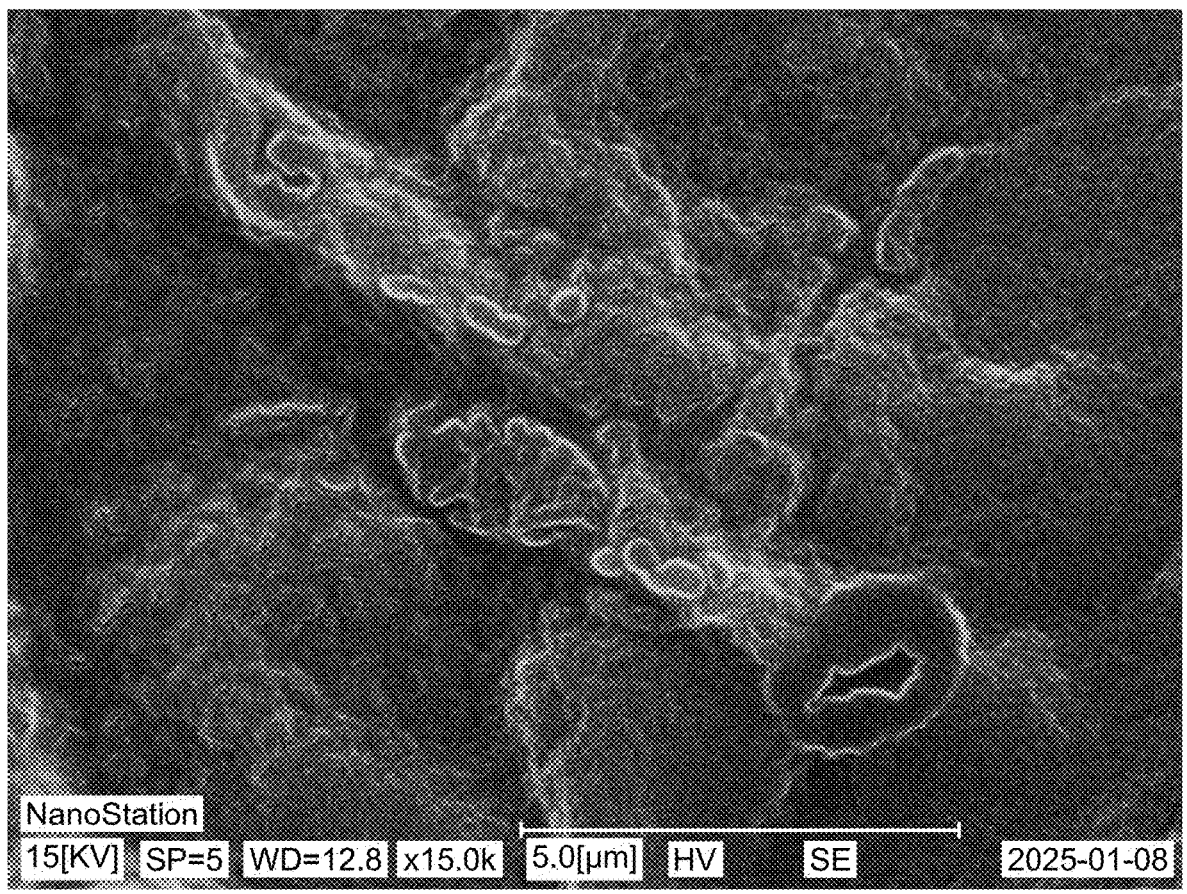
FIGS. 7A-7E show SEM images of bacterial colonies grown on FBCU agar media, according to certain embodiments.
Figure 7B:
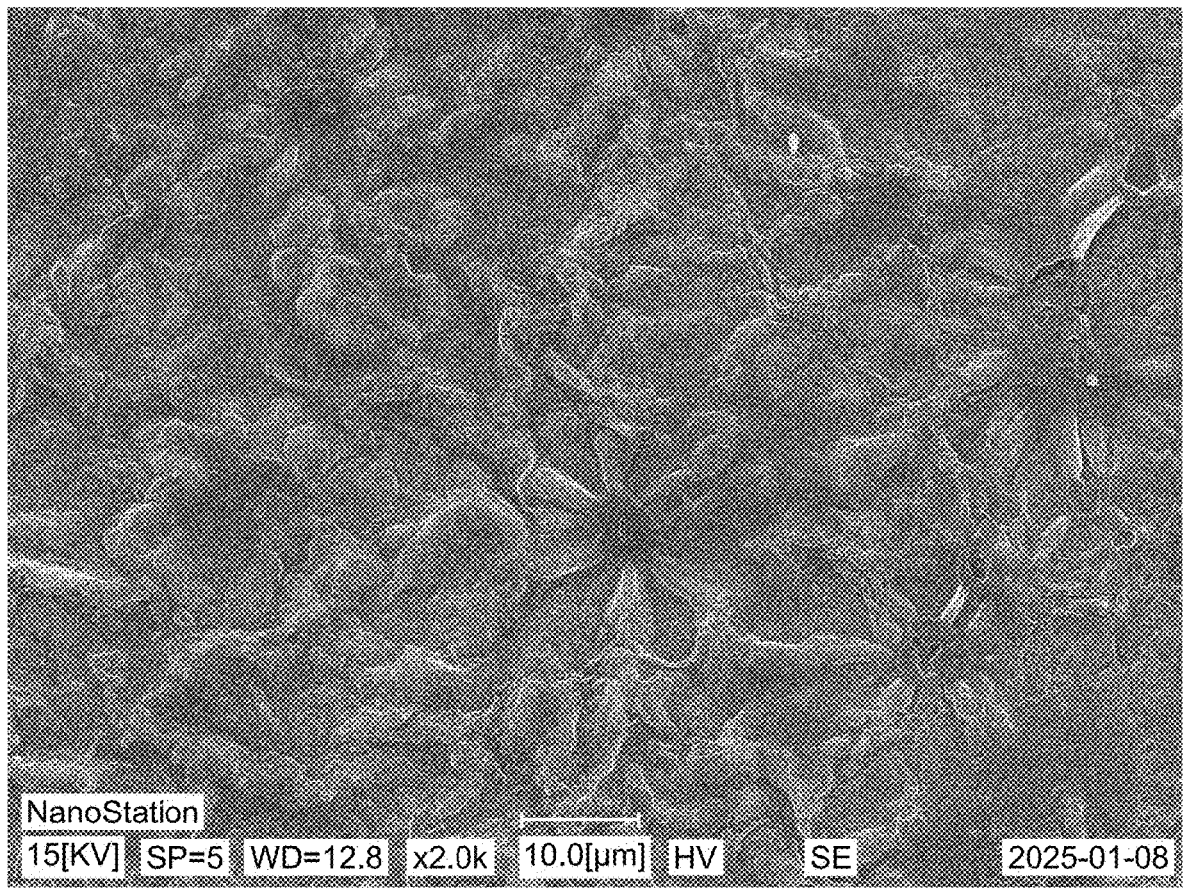
Figure 7C:
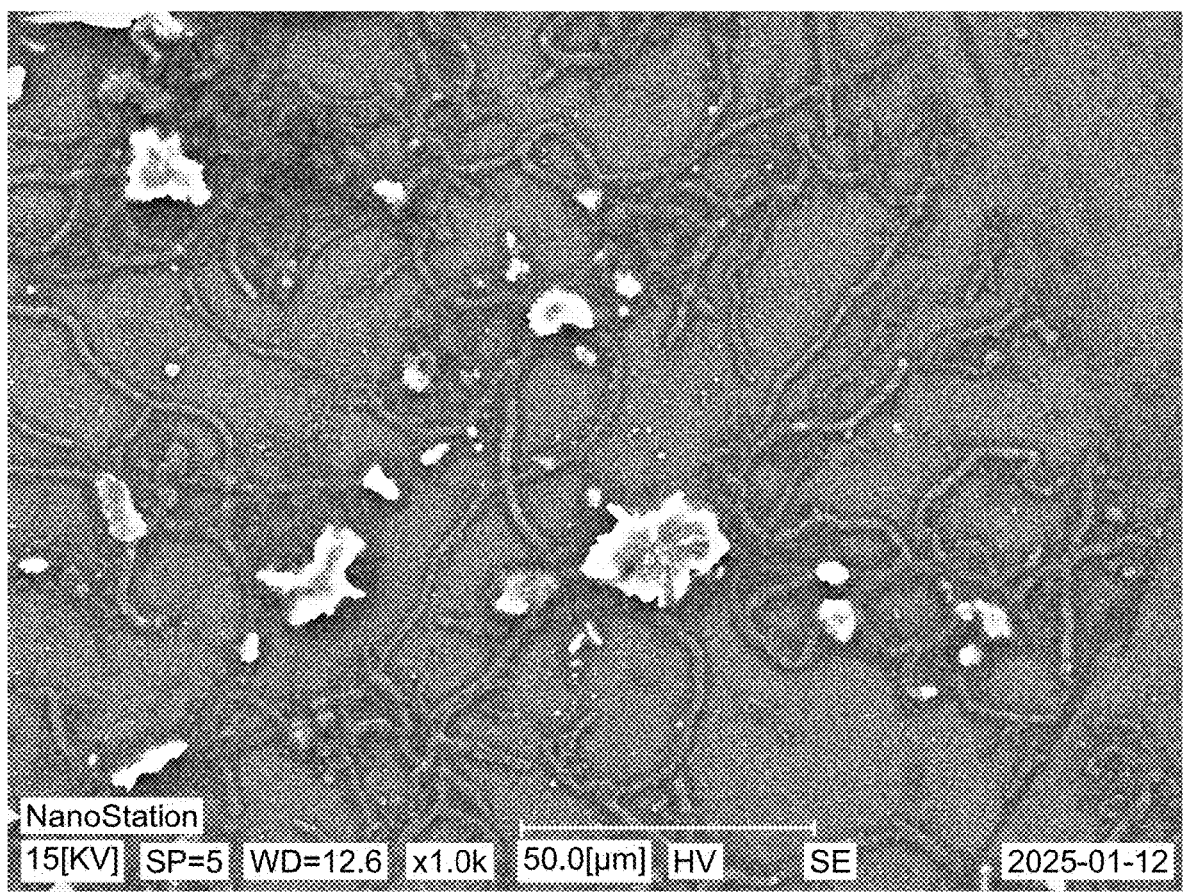
Figure 7D:
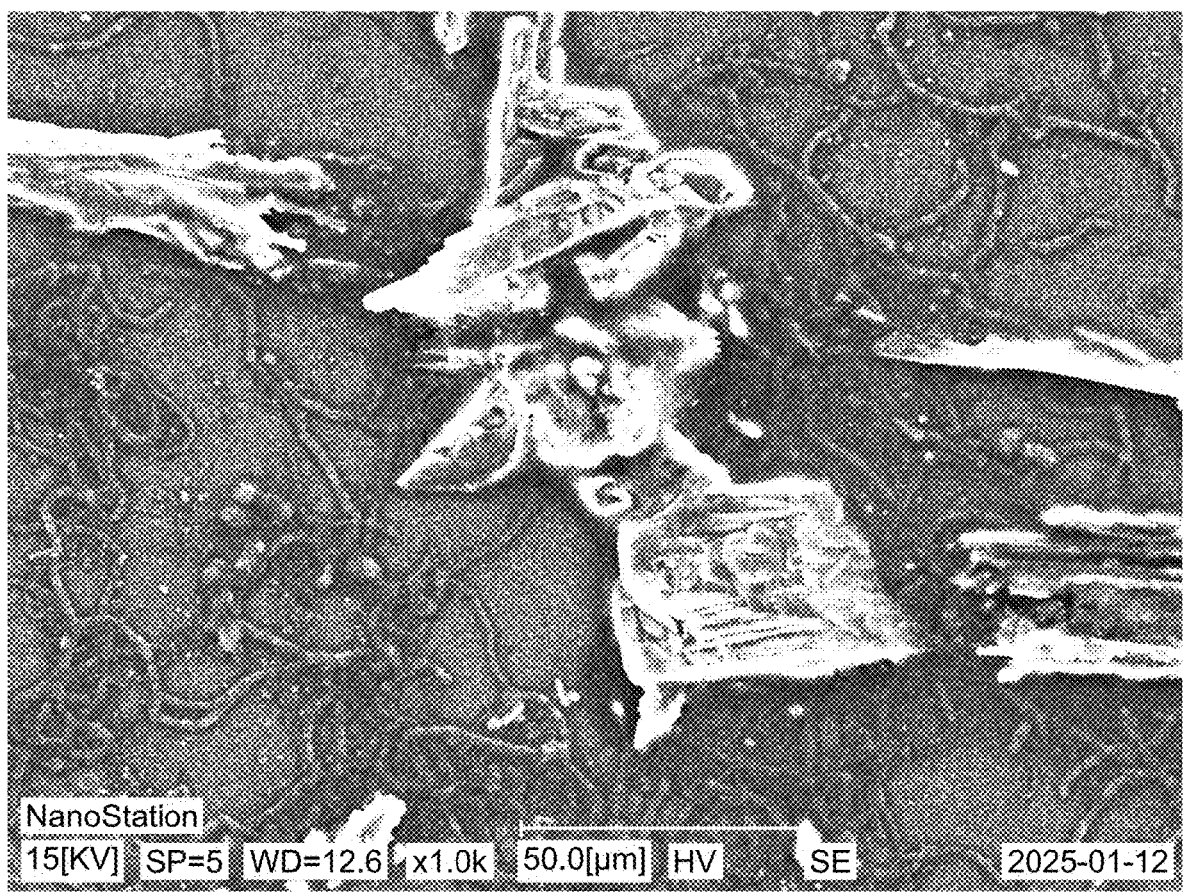
Figure 7E:
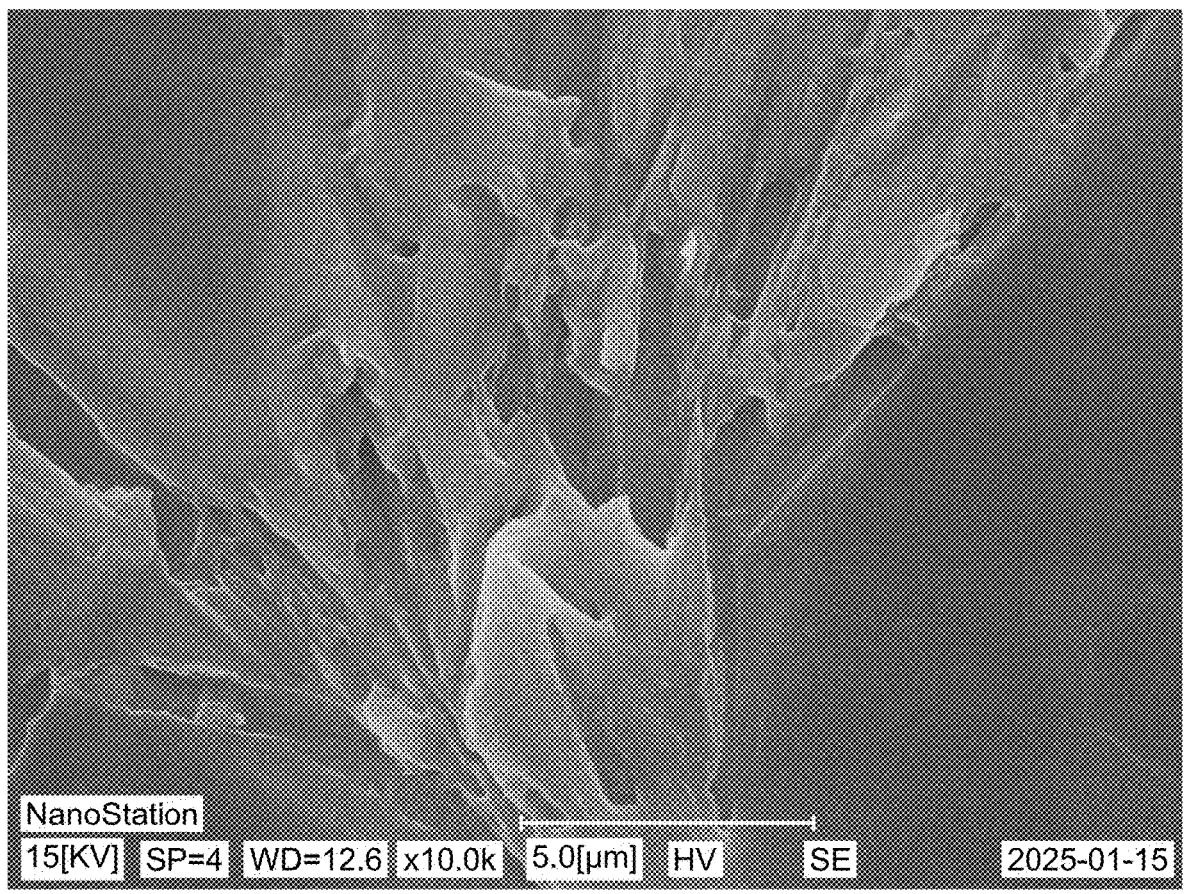

Enrichment 1 mL sample was used for isolation on a solid medium. Aliquots (1 to 10) and 10 dilutions were plated onto a 2% agar formation brine medium with crude oil (1% v/v) and natural plant oils (including fats and fatty acids) (1% v/v) used as carbon sources. The solution was stirred until the added materials were dissolved and sterilized by autoclaving at 121° C. for 20 minutes. Thereafter, 10 mL portions of the solution were poured into 60×15 mm plastic petri dishes. Upon cooling to room temperature, the solution in the petri dishes gelled, forming the medium. The physical appearance of the medium should have an adequate gel; growth is poor, and the colonies are small if the gel in the Petri dishes is too hard; conversely, a soft medium is difficult to work with as it tends to tear. The plates were incubated at 55° C. for 7 days, until colony formation. FIG. 3 is a pictorial image of bacterial colonies grown on *Fusobacterium* Selective Agar (FBFA) media; FIG. 4 is a pictorial image of bacterial colonies grown on FBCU agar media; FIG. 5 is a pictorial image of bacterial colonies grown on FBFACU agar media; and FIG. 6 is a pictorial image of the isolated pure bacterial strains grown in bacterial colonies in FBNB agar media.

TABLE 2

Composition of the culture media used for culturing

| Ingredients | FBFA media (g/L) | FBCU media (g/L) | FBFACU media (g/L) | FBNB media (g/L) |
| --- | --- | --- | --- | --- |
| NaCl | 150.46 | 150.46 | 150.46 | 150.46 |
| $Na_2SO_4$ | 0.5175 | 0.5175 | 0.5175 | 0.5175 |
| $NaHCO_3$ | 0.4874 | 0.4874 | 0.4874 | 0.4874 |
| $CaCl_2$ dihydrate | 68.823 | 68.823 | 68.823 | 68.823 |
| $MgCl_2 \cdot 6H_2O$ | 20.395 | 20.395 | 20.395 | 20.395 |
| Peptone | — | — | — | 3 |
| Yeast extract | — | — | — | 5 |
| Plant Oils | 1% v/v | — | 1% v/v | — |
| Crude oil | — | 1% v/v | 1% v/v | — |
| Agar | 20 | 20 | 20 | 20 |
| DI water in mL | 758.32 | 758.32 | 758.32 | 758.32 |

Single colonies were picked and used for screening. Individual colonies were purified by repeated streaking on agar formation brine medium containing 1% (v/v) crude oil plates. The strains' purity, shape, and size were analyzed using an Olympus CX21FS1 binocular microscope. FIG. 3 is a pictorial image of bacterial colonies grown on *Fusobacterium* Selective Agar (FBFA) media, according to certain embodiments. FIG. 4 is a pictorial image of bacterial colonies grown on FBCU agar media, according to certain embodiments. FIG. 5 is a pictorial image of bacterial colonies grown on FBFACU agar media, according to certain embodiments. FIG. 6 is a pictorial image of the isolated pure bacterial strains grown in bacterial colonies in FBNB agar media, according to certain embodiments. FIGS. 7A-7E show SEM images of bacterial colonies grown on FBCU agar media, according to certain embodiments.

Numerous modifications and variations of the present disclosure are possible in light of the above teachings. It is therefore to be understood that within the scope of the appended claims, the invention may be practiced otherwise than as specifically described herein.

The invention claimed is:

1. A method of microbially enhanced oil recovery, the method comprising culturing a salt-tolerant bacteria using a high-salt cell culture medium comprising sodium chloride present in an amount of 140 to 160 g per liter of high-salt cell culture medium,
sodium sulfate present in an amount of 0.40 to 0.60 g per liter of high-salt cell culture medium,
sodium bicarbonate present in an amount of 0.38 to 0.59 g per liter of high-salt cell culture medium,
calcium chloride present in an amount of 60 to 80 g per liter of high-salt cell culture medium,
magnesium chloride present in an amount of 10 to 31 g per liter of high-salt cell culture medium,
agar present in an amount of 10 to 30 g per liter of high-salt cell culture medium,
glycerol present in an amount of 1 to 5 vol %, and
water, each based on a total volume of high-salt cell culture medium; suspending the salt-tolerant bacteria in a liquid medium comprising
sodium chloride present in an amount of 140 to 160 g per liter of liquid medium,
sodium sulfate present in an amount of 0.40 to 0.60 g per liter of liquid medium,
sodium bicarbonate present in an amount of 0.38 to 0.59 g per liter of liquid medium,
calcium chloride present in an amount of 60 to 80 g per liter of liquid medium,
magnesium chloride present in an amount of 10 to 31 g per liter of liquid medium,
glycerol present in an amount of 1 to 5 vol %, and
water, each based on a total volume of liquid medium, to form a first broth;
incubating the first broth to form an inoculation mixture;
mixing the inoculation mixture with a production water in a volume ratio of 1:1 to form a bacteria-containing liquid mixture;
propagating the bacteria-containing liquid mixture in a portion of a subterranean geological formation containing an oil deposit; and
recovering oil in the oil deposit.

2. The method of claim 1,
wherein the recovering comprises:
  producing a production mixture comprising the oil in the oil deposit the bacteria-containing liquid mixture;
  recovering to a surface the production mixture; and
  separating the oil and the bacteria-containing liquid mixture, and
wherein the high-salt cell culture medium further comprises a nutrient supplement which is at least one selected from the group consisting of
a plant oil mixture comprising
  12.5 to 17.5 wt. % saturated fatty acids,
  17.5 to 22.5 wt. % monounsaturated fatty acids,
  25 to 35 wt. % polyunsaturated fatty acids, and
  triglycerides, each based on a total weight of plant oil mixture; and
a nutrient mixture comprising
  2 to 4 g peptone per liter of high-salt cell culture medium, and
  4.0 to 6.0 g yeast extract per liter of high-salt cell culture medium.

3. The method of claim 2, wherein the plant oil mixture present in an amount of 0.25 to 2.5 vol. % based on a total volume of high-salt cell culture medium.

4. The method of claim 1, further comprising, prior to the culturing, deoxygenating the high-salt cell culture medium by bubbling nitrogen gas which is substantially free of oxygen through the high-salt cell culture medium.

5. The method of claim 1, further comprising, prior to the culturing, sterilizing the high-salt cell culture medium by autoclaving a non-sterile volume of the high-salt cell culture medium at 115 to 130° C. and 5 to 25 psi for 10 to 60 minutes.

6. The method of claim 1, wherein the culturing is performed at 40 to 70° C. for 1 to 14 days.

7. The method of claim 1, wherein the culturing is performed under anaerobic conditions.

8. The method of claim 1, wherein the high-salt cell culture medium further comprises crude oil present in an amount of 0.25 to 2.5 vol. % based on a total volume of high-salt cell culture medium.

9. The method of claim 1, wherein the liquid medium further comprises a nutrient supplement which is at least one selected from the group consisting of
a plant oil mixture comprising
  12.5 to 17.5 wt. % saturated fatty acids,
  17.5 to 22.5 wt. % monounsaturated fatty acids,
  25 to 35 wt. % polyunsaturated fatty acids, and
  triglycerides, each based on a total weight of plant oil mixture; and
a nutrient mixture comprising
  2 to 4 g peptone per liter of liquid medium, and
  4.0 to 6.0 g yeast extract per liter of liquid medium.

10. The method of claim 9, wherein the plant oil mixture present in an amount of 0.25 to 2.5 vol. % based on a total volume of liquid medium.

11. The method of claim 1, wherein the incubating is performed at 45 to 75° C. for 30 to 120 days.

12. The method of claim 1, wherein the incubating is performed under anaerobic conditions.

13. The method of claim 1, wherein the liquid medium further comprises crude oil present in an amount of 1 to 40 vol. % based on a total volume of liquid medium.

14. The method of claim 1, further comprising, prior to the incubating, deoxygenating the liquid medium by bubbling nitrogen gas which is substantially free of oxygen through the liquid medium.

15. The method of claim 1, further comprising, prior to the incubating, sterilizing the liquid medium by autoclaving a non-sterile volume of the liquid medium at 115 to 130° C. and 5 to 25 psi for 10 to 60 minutes.

16. The method of claim 1, wherein the production water has a salinity of 350,000 ppm to 5,000,000 ppm.

17. The method of claim 1, further comprising, following the propagating the bacteria-containing liquid mixture in a portion of a subterranean geological formation containing an oil deposit, pumping into the subterranean geological formation nitrogen gas which is substantially free of oxygen.

18. The method of claim 1, further comprising adding to the production water a nutrient supplement which is at least one selected from the group consisting of
a plant oil mixture comprising
  12.5 to 17.5 wt. % saturated fatty acids,
  17.5 to 22.5 wt. % monounsaturated fatty acids,
  25 to 35 wt. % polyunsaturated fatty acids, and
  triglycerides, each based on a total weight of plant oil mixture; and
a nutrient mixture comprising
  2 to 4 g peptone per liter of nutrient supplement, and
  4.0 to 6.0 g yeast extract per liter of nutrient supplement.

19. The method of claim 1, wherein the salt-tolerant bacteria is a member of a genus selected from *streptococcus, bacillus*, and *halomonas*.

20. The method of claim 1, wherein the bacteria-containing liquid mixture comprises
  a salt-tolerant bacteria from the genus *streptococcus,*
  a salt-tolerant bacteria from the genus *bacillus*, and
  a salt-tolerant bacteria from the genus *halomonas*.

* * * * *